United States Patent
Cooper et al.

(10) Patent No.: US 8,344,000 B2
(45) Date of Patent: Jan. 1, 2013

(54) COMPOUNDS WHICH HAVE ACTIVITY AT $M_1$ RECEPTOR AND THEIR USES IN MEDICINE

(75) Inventors: David Gwyn Cooper, Harlow (GB); Ian Thomson Forbes, Harlow (GB); Vincenzo Garzya, Harlow (GB); Dale James Johnson, Harlow (GB); Paul Adrian Wyman, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 343 days.

(21) Appl. No.: 12/678,360

(22) PCT Filed: Sep. 18, 2008

(86) PCT No.: PCT/EP2008/062398
§ 371 (c)(1),
(2), (4) Date: Mar. 16, 2010

(87) PCT Pub. No.: WO2009/037293
PCT Pub. Date: Mar. 26, 2009

(65) Prior Publication Data
US 2011/0130423 A1 Jun. 2, 2011

(30) Foreign Application Priority Data
Sep. 20, 2007 (GB) .................... 0718415.3

(51) Int. Cl.
C07D 401/14 (2006.01)
A61K 31/454 (2006.01)
A61P 25/18 (2006.01)
A61P 25/28 (2006.01)

(52) U.S. Cl. ........................ 514/321; 546/198
(58) Field of Classification Search ............... 546/198; 514/321
See application file for complete search history.

(56) References Cited

U.S. PATENT DOCUMENTS

| | | | |
|---|---|---|---|
| 3,161,645 A | 12/1964 | Adriaan et al. |
| 3,989,707 A | 11/1976 | Janssen et al. |
| 4,470,989 A | 9/1984 | Henning et al. |
| 5,574,044 A | 11/1996 | Thompson et al. |
| 5,691,323 A | 11/1997 | Thompson et al. |
| 5,977,134 A | 11/1999 | Ciccarone et al. |
| 6,162,804 A | 12/2000 | Bilodeau et al. |
| 6,465,484 B1 | 10/2002 | Bilodeau et al. |
| 6,872,733 B2 | 3/2005 | Goehring et al. |
| 6,951,849 B2 | 10/2005 | Kelly et al. |
| 7,087,593 B2 | 8/2006 | Kelly et al. |
| 7,598,393 B2 | 10/2009 | Kon-I et al. |
| 7,776,885 B2 | 8/2010 | Katsu et al. |
| 2002/0019395 A1 | 2/2002 | Zhu et al. |
| 2003/0008886 A1 | 1/2003 | Goehring et al. |
| 2003/0040513 A1 | 2/2003 | Baxter et al. |
| 2003/0100545 A1 | 5/2003 | Kelly et al. |
| 2004/0067931 A1 | 4/2004 | Kelly et al. |
| 2005/0020575 A1 | 1/2005 | Cole et al. |
| 2005/0192307 A1 | 9/2005 | Goehring et al. |
| 2006/0025402 A1 | 2/2006 | Kelly et al. |
| 2006/0199799 A1 | 9/2006 | Kelly et al. |
| 2006/0205785 A1 | 9/2006 | Kelly et al. |
| 2006/0258707 A1 | 11/2006 | Kelly et al. |
| 2008/0103178 A1 | 5/2008 | Hashimoto et al. |
| 2008/0293770 A1 | 11/2008 | Budzik et al. |
| 2008/0306112 A1 | 12/2008 | Budzik et al. |

FOREIGN PATENT DOCUMENTS

| | | | |
|---|---|---|---|
| EP | 0068261 A1 | 1/1983 |
| EP | 0491212 A1 | 6/1992 |
| EP | 1221443 A1 | 7/2002 |
| EP | 1386920 A1 | 2/2004 |
| EP | 149212 A | 12/2004 |
| WO | WO96/13262 | 5/1996 |
| WO | WO97/16189 A | 5/1997 |
| WO | 9932481 | * 7/1999 |
| WO | WO99/32481 | 7/1999 |
| WO | WO03/105781 | 12/2003 |
| WO | WO2004/054974 A | 7/2004 |

(Continued)

OTHER PUBLICATIONS

Jassen, et al. "Benzimidazolinon . . . " CA 84:135657 (1976).
Henniung, et al. "N-oxazyclyl alkylpiperidine . . . " CA 98:160727 (1983).
Sur, et al. "Selective targeting of Muscarinic . . . " Current Neuropharm. V. 3 p. 63-71 (2005).
Burgey et al, "Benzodiazepine calcitonin gene-related peptide (CGRP) receptor antagonists: Optimization of the 4-substituted piperidine" Bioorganic & Medicinal Chemistry Letters, vol. 16, No. 19, Oct. 1, 2006 pp. 5052-5056.

(Continued)

*Primary Examiner* — Niloofar Rahmani
(74) *Attorney, Agent, or Firm* — Linda E. Hall; John L. Lemanowicz

(57) ABSTRACT

Compounds of formula (I) and salts thereof are provided:

wherein $R^4$, $R^5$, $R^6$, Q, A, and Y are as defined in the description. Uses of the compounds as medicaments and in the manufacture of medicaments for treating psychotic disorders, cognitive impairments and Alzheimer's Disease are disclosed. The invention further discloses pharmaceutical compositions comprising the compounds.

10 Claims, No Drawings

FOREIGN PATENT DOCUMENTS

| | | |
|---|---|---|
| WO | WO2004/089942 | 10/2004 |
| WO | WO2007/036711 | 4/2007 |
| WO | WO2007/036715 | 4/2007 |
| WO | WO2007/036718 | 4/2007 |
| WO | WO2008/119711 | 10/2008 |
| WO | WO2008/119712 | 10/2008 |
| WO | WO2008/119713 | 10/2008 |
| WO | WO2008/119714 | 10/2008 |
| WO | WO2008/119715 | 10/2008 |
| WO | WO2008/119716 | 10/2008 |
| WO | WO2008/119717 | 10/2008 |
| WO | WO2008/119718 | 10/2008 |
| WO | WO2008/119719 | 10/2008 |
| WO | WO2008/119720 | 10/2008 |
| WO | WO2008/119721 | 10/2008 |

OTHER PUBLICATIONS

Gustin D. J. et al: "Discovery and SAR studies of a novel series of noncovalent cathepsin S inhibitors" Bioorganic & Medicinal Chemistry Letters, vol. 15, No. 6, Mar. 15, 2005 pp. 1687-1691.

Hennings, R., et al: "Synthesis and neuroleptic activity of a series of 1-[1-(benzo-1,4-dioxan-2-ylmethyl)-4-piperidinyl] benzimidazolone derivatives". Journal of Medicinal Chemistry, vol. 30, No. 5, May 1987 pp. 814-819.

Poulain R., et al.: "From hit to lead. Analyzing structure-profile relationships" Journal of Medicinal Chemistry, vol. 44, Sep. 11, 2001, pp. 3391-3401.

Poulain, R., et al: "From hit to lead." Journal of Medicinal Chemistry, vol. 44 No. 21, Oct. 2001, pp. 3378-3390.

Rossi, A., et al: "Benzimidazol-Derivate and verwandte Heterocyclen V. Die Kondensation von o-Phenylendiamine mit aliphatischen and alicyclischen beta-Ketoestern" Helvetica Chimica Acta, vol. 43, No. 5, Aug. 1, 1960, pp. 1298-1313.

\* cited by examiner

COMPOUNDS WHICH HAVE ACTIVITY AT $M_1$ RECEPTOR AND THEIR USES IN MEDICINE

This application is a 371 of International Application No. PCT/EP2008/062398, filed 18 Sep. 2008, which claims the priority of GB Application No. 0718415.3, filed 20 Sep. 2007, which are incorporated herein in their entirety.

This invention relates to novel compounds, pharmaceutical compositions containing them and their use in therapy, in particular as antipsychotic agents, as agents for the treatment of cognitive impairment associated with schizophrenia, and as agents for treatment of Alzheimer's Disease.

Muscarinic acetylcholine receptors are members of the G protein coupled receptor superfamily which mediate the actions of the neurotransmitter acetylcholine in both the central and peripheral nervous system. Five muscarinic receptor subtypes have been cloned, $M_1$ to $M_5$. The muscarinic $M_1$ receptor is predominantly expressed in the cerebral cortex and hippocampus, although it is also expressed in the periphery e.g. exocrine glands.

Muscarinic receptors in the central nervous system, especially $M_1$, play a critical role in mediating higher cognitive processing. Diseases associated with cognitive impairments, such as Alzheimer's disease, are accompanied by loss of cholinergic neurons in the basal forebrain. Furthermore, in animal models, blockade or lesion of central cholinergic pathways results in profound cognitive deficits.

Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to side effects resulting from stimulation of peripheral muscarinic receptors including disturbed gastrointestinal motility and nausea.

The dopamine hypothesis of schizophrenia suggests that excess dopaminergic stimulation is responsible for the positive symptoms of the disease, hence the utility of dopamine receptor antagonists to reduce psychotic symptoms. However, conventional dopamine receptor antagonists can cause extrapyramidal side effects (EPS) in patients, including tremor and tardive dyskinesias.

$M_1$ receptor agonists have been sought for the symptomatic treatment of cognitive decline. More recently, a number of groups have shown that muscarinic receptor agonists display an atypical antipsychotic-like profile in a range of pre-clinical paradigms. The muscarinic agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine-induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile.

Xanomeline has also been shown to reduce psychotic symptoms such as suspiciousness, hallucinations and delusions in Alzheimer's patients and has subsequently been assessed in a small phase II trial in schizophrenic patients where it showed a trend to improvement in PANSS and separation from placebo in a cognitive readout. However, the relatively non-selective nature of the compound gives rise to dose-limiting peripheral cholinergic side effects.

Over-production of β amyloid is a critical pathogenic event in Alzheimer's Disease (AD) and data have been published showing that $M_1$ receptor agonists modulate the processing of β-APP, the precursor of β amyloid, to increase the production of sAPPα (non-amyloidogenic). Subsequent studies have demonstrated that this event is accompanied by a decreased secretion of 13 amyloid (for review see Current Opinion in Investigational Drugs, 2002, 3 (11), 1633-1636). In addition, it has recently been reported that an $M_1$ receptor agonist can affect APP processing toward the non-amyloidogenic pathway, in vivo (Neuron, 2006, 49, 671-682). Thus $M_1$ selective agonists have potential for a preventative/disease modifying role in AD therapy.

Certain $M_1$ receptor agonists are known, for example in PCT/GB2006/003590, PCT/GB2006/003595 and PCT/GB2006/003585. We have now found a novel group of compounds which are $M_1$ receptor agonists.

In a first aspect therefore, the invention provides a compound of formula (I) or a salt thereof:

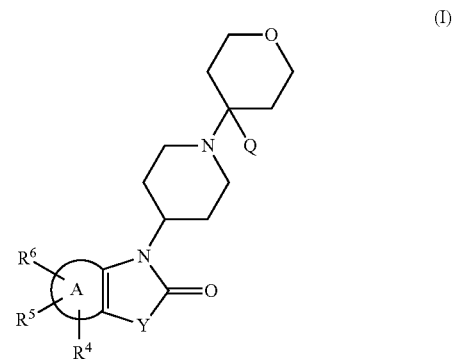

wherein:
$R^4$, $R^5$ and $R^6$ are independently selected from hydrogen, halogen, $C_{1-6}$alkyl, $C_{1-6}$alkyl substituted with one or more fluorine atoms, cyano, $C_{1-6}$alkylsulfonyl, $C_{1-6}$alkylsulfonyl substituted with one or more fluorine atoms, $C_{3-6}$cycloalkyl, $C_{1-6}$alkoxy, $C_{1-6}$alkoxy substituted with one or more fluorine atoms, $C_{1-6}$alkanoyl, —C(=NOC$_{1-6}$alkyl)C$_{1-6}$alkyl, $C_{1-6}$alkoxyC$_{1-6}$alkyl, and —C(O)NR$_a$R$_b$;

$R_a$ and $R_b$ are each independently hydrogen or $C_{1-6}$alkyl, or together with the nitrogen atom to which they are attached form a five or six membered ring;

ring A is a benzene ring or 6-membered aromatic heterocylic ring containing one or two nitrogen atoms;

Q is selected from hydrogen and $C_{1-6}$alkyl; and

Y is selected from O, S, $CH_2$, CHF, $CF_2$, CHMe, $C(Me)_2$, $CH_2CH_2$, $OCH_2$, and $CH_2O$.

As used herein, the term "alkyl" refers to a straight or branched hydrocarbon chain containing the specified number of carbon atoms. For example, "$C_{1-6}$alkyl" means a straight or branched alkyl containing at least 1, and at most 6, carbon atoms. Examples of "$C_{1-6}$alkyl" include, but are not limited to, methyl, ethyl, n-propyl, n-butyl, n-pentyl, n-hexyl, isobutyl, isopropyl, t-butyl and 1,1-dimethylpropyl. "$C_{1-4}$alkyl" means a straight or branched alkyl containing at least 1, and at most 4, carbon atoms. Examples of "$C_{1-4}$alkyl" include, but are not limited to, methyl, ethyl, n-propyl, n-butyl, isobutyl, isopropyl, and t-butyl.

As used herein, the term "alkoxy" refers to the group "O-alkyl" where "alkyl" is as hereinbefore defined. For example, "$C_{1-6}$alkoxy" means a straight or branched alkoxy group containing at least 1, and at most 6, carbon atoms.

Examples of "$C_{1-6}$alkoxy" as used herein include, but are not limited to, methoxy, ethoxy, propoxy, prop-2-oxy, butoxy, but-2-oxy, 1-methylethyl-oxy, 2-methylprop-1-oxy, 2-methylprop-2-oxy, pentoxy or hexyloxy.

As used herein, the term "cycloalkyl" refers to a non-aromatic hydrocarbon ring containing the specified number of carbon atoms. For example, "$C_{3-6}$cycloalkyl" means a non-aromatic carbocyclic ring containing at least three, and at most six, ring carbon atoms. Examples of "$C_{3-6}$cycloalkyl" as used herein include, but are not limited to, cyclopropyl, cyclobutyl, cyclopentyl and cyclohexyl.

As used herein, the term "halogen" (or the abbreviated form "halo") refers to the elements fluorine (which may be abbreviated to "fluoro" or "F"), chlorine (which may be abbreviated to "chloro" or "Cl"), bromine (which may be abbreviated to "bromo" or "Br") and iodine (which may be abbreviated to "iodo" or "I"). Examples of halogens are fluorine, chlorine and bromine.

As used herein, the term "$C_{1-6}$alkylsulfonyl" refers to a group $SO_2$—$C_{1-6}$alkyl, wherein $C_{1-6}$alkyl is as hereinbefore defined. Examples of "$C_{1-6}$alkylsulfonyl" as used herein include, but are not limited to, methylsulphonyl, ethylsulphonyl, propylsulphonyl, butylsulphonyl, pentylsulphonyl and hexylsulphonyl.

As used herein, the term "$C_{1-6}$alkanoyl" refers to a group —C(O)$C_{1-6}$alkyl wherein $C_{1-6}$alkyl is as hereinbefore defined. Examples of "$C_{1-6}$alkanoyl" as use herein include, but are not limited to, methanoyl, ethanoyl, propanoyl, butanoyl, pentanoyl and hexanoyl.

As used herein, the term "$C_{1-6}$alkoxy$C_{1-6}$alkyl" refers to a group $C_{1-6}$alkyl-O—$C_{1-6}$alkyl wherein $C_{1-6}$alkyl is as hereinbefore defined. Examples of "$C_{1-6}$alkoxy$C_{1-6}$alkyl" as used herein include, but are not limited to, methoxymethyl, methoxyethyl, methoxypropyl, methoxybutyl, methoxypentyl, methoxyhexyl, ethoxymethyl, ethoxyethyl, ethoxypropyl, ethoxybutyl, ethoxypentyl, and ethoxyhexyl.

As used herein, the term "substituted" refers to substitution with the named substituent or substituents, multiple degrees of substitution being allowed unless otherwise stated. For example, there may be 1, 2 or 3 substituents on a given substituted group. For example, if $R^6$ is a $C_{1-6}$alkyl group, it may be substituted with one, 2, 3 or 4 fluoro groups; and if $R^6$ is a $C_{1-6}$alkoxy group, it may be substituted with one, 2, 3 or 4 fluoro groups.

In one embodiment $R^4$ is selected from hydrogen, halogen, $C_{1-4}$alkyl, $C_{1-4}$alkyl substituted with one or more fluorine atoms, cyano, $C_{1-4}$alkylsulfonyl, $C_{1-4}$alkylsulfonyl substituted with one or more fluorine atoms, $C_{3-6}$cycloalkyl, $C_{1-4}$alkoxy, $C_{1-4}$alkoxy substituted with one or more fluorine atoms, $C_{1-4}$alkanoyl, —C(=NOC$_{1-4}$alkyl)$C_{1-4}$alkyl, $C_{1-4}$alkoxy$C_{1-4}$alkyl, and —C(O)NR$_a$R$_b$.

In one embodiment, $R^4$ is selected from hydrogen, halogen, $C_{1-2}$alkyl, $C_{1-2}$alkyl substituted with one or more fluorine atoms, cyano, $C_{1-2}$alkylsulfonyl, $C_{1-2}$alkylsulfonyl substituted with one or more fluorine atoms, $C_{3-6}$cycloalkyl, $C_{1-2}$alkoxy, $C_{1-2}$alkoxy substituted with one or more fluorine atoms, $C_{1-2}$alkanoyl, —C(=NOC$_{1-2}$alkyl)$C_{1-2}$alkyl, $C_{1-2}$alkoxy$C_{1-2}$alkyl, and —C(O)NR$_a$R$_b$.

In one embodiment $R^4$ is selected from hydrogen and halogen.

In one embodiment $R^4$ is selected from hydrogen and fluorine.

In one embodiment, $R^4$ is hydrogen.

In one embodiment $R^4$ is fluorine.

In one embodiment $R^5$ is selected from hydrogen, halogen, $C_{1-4}$alkyl, $C_{1-4}$alkyl substituted with one or more fluorine atoms, cyano, $C_{1-4}$alkylsulfonyl, $C_{1-4}$alkylsulfonyl substituted with one or more fluorine atoms, $C_{3-6}$cycloalkyl, $C_{1-4}$alkoxy, $C_{1-4}$alkoxy substituted with one or more fluorine atoms, $C_{1-4}$alkanoyl, —C(=NOC$_{1-4}$alkyl)$C_{1-4}$alkyl, $C_{1-4}$alkoxy$C_{1-4}$alkyl, and —C(O)NR$_a$R$_b$.

In one embodiment, $R^5$ is selected from hydrogen, halogen, $C_{1-2}$alkyl, $C_{1-2}$alkyl substituted with one or more fluorine atoms, cyano, $C_{1-2}$alkylsulfonyl, $C_{1-2}$alkylsulfonyl substituted with one or more fluorine atoms, $C_{3-6}$cycloalkyl, $C_{1-2}$alkoxy, $C_{1-2}$alkoxy substituted with one or more fluorine atoms, $C_{1-2}$alkanoyl, —C(=NOC$_{1-2}$alkyl)$C_{1-2}$alkyl, $C_{1-2}$alkoxy$C_{1-2}$alkyl, and —C(O)NR$_a$R$_b$.

In one embodiment $R^5$ is selected from hydrogen and halogen.

In one embodiment $R^5$ is selected from hydrogen and fluorine.

In one embodiment, $R^5$ is hydrogen.

In one embodiment $R^5$ is fluorine.

In one embodiment $R^6$ is selected from hydrogen, halogen, $C_{1-6}$alkyl, $C_{1-6}$alkyl substituted with one or more fluorine atoms, cyano, $C_{1-6}$alkylsulfonyl, $C_{1-6}$alkylsulfonyl substituted with one or more fluorine atoms, $C_{3-6}$cycloalkyl, $C_{1-6}$alkoxy, $C_{1-6}$alkoxy substituted with one or more fluorine atoms, $C_{1-6}$alkanoyl, —C(=NOC$_{1-6}$alkyl)$C_{1-6}$alkyl, $C_{1-6}$alkoxy$C_{1-6}$alkyl, and —C(O)NR$_a$R$_b$; provided that when $R^6$ is selected from hydrogen, $C_{1-6}$alkyl, $C_{1-6}$alkoxy, and halogen then $R^4$ and $R^5$ are not both hydrogen.

In one embodiment $R^6$ is selected from hydrogen, halogen, $C_{1-4}$alkyl, $C_{1-4}$alkyl substituted with one or more fluorine atoms, cyano, $C_{1-4}$alkylsulfonyl, $C_{1-4}$alkylsulfonyl substituted with one or more fluorine atoms, $C_{3-6}$cycloalkyl, $C_{1-4}$alkoxy, $C_{1-4}$alkoxy substituted with one or more fluorine atoms, $C_{1-4}$alkanoyl, —C(=NOC$_{1-4}$alkyl)$C_{1-4}$alkyl, $C_{1-4}$alkoxy$C_{1-4}$alkyl, and —C(O)NR$_a$R$_b$.

In one embodiment, $R^6$ is selected from hydrogen, halogen, $C_{1-4}$alkyl, $C_{1-4}$alkyl substituted with one or more fluorine atoms, cyano, $C_{1-4}$alkylsulfonyl, $C_{1-4}$alkylsulfonyl substituted with one or more fluorine atoms, $C_{3-6}$cycloalkyl, $C_{1-4}$alkoxy, $C_{1-4}$alkoxy substituted with one or more fluorine atoms, $C_{1-4}$alkanoyl, —C(=NOC$_{1-4}$alkyl)$C_{1-4}$alkyl, $C_{1-4}$alkoxy$C_{1-4}$alkyl, and —C(O)NR$_a$R$_b$; provided that when $R^6$ is selected from hydrogen, $C_{1-4}$alkyl, $C_{1-4}$alkoxy and halo, then $R^4$ and $R^5$ are not both hydrogen.

In one embodiment, $R^6$ is selected from hydrogen, halogen, $C_{1-2}$alkyl, $C_{1-2}$alkyl substituted with one or more fluorine atoms, cyano, $C_{1-2}$alkylsulfonyl, $C_{1-2}$alkylsulfonyl substituted with one or more fluorine atoms, $C_{3-6}$cycloalkyl, $C_{1-2}$alkoxy, $C_{1-2}$alkoxy substituted with one or more fluorine atoms, $C_{1-2}$alkanoyl, —C(=NOC$_{1-2}$alkyl)$C_{1-2}$alkyl, $C_{1-2}$alkoxy$C_{1-2}$alkyl, and —C(O)NR$_a$R$_b$.

In one embodiment, $R^6$ is selected from hydrogen, halogen, $C_{1-2}$alkyl, $C_{1-2}$alkyl substituted with one or more fluorine atoms, cyano, $C_{1-2}$alkylsulfonyl, $C_{1-2}$alkylsulfonyl substituted with one or more fluorine atoms, $C_{3-6}$cycloalkyl, $C_{1-2}$alkoxy, $C_{1-2}$alkoxy substituted with one or more fluorine atoms, $C_{1-2}$alkanoyl, —C(=NOC$_{1-2}$alkyl)$C_{1-2}$alkyl, $C_{1-2}$alkoxy$C_{1-2}$alkyl, and —C(O)NR$_a$R$_b$; provided that when $R^6$ is selected from hydrogen, $C_{1-2}$alkyl, $C_{1-2}$alkoxy and halo, then $R^4$ and $R^5$ are not both hydrogen.

In one embodiment $R^6$ is selected from hydrogen, $C_{1-2}$alkyl, and $C_{1-2}$alkyl substituted with one or more fluorine atoms.

In one embodiment, $R^6$ is selected from hydrogen, $C_{1-2}$alkyl, and $C_{1-2}$alkyl substituted with one or more fluorine atoms; provided that when $R^6$ is selected from hydrogen and $C_{1-2}$alkyl, $R^4$ and $R^5$ are not both hydrogen.

In one embodiment $R^6$ is selected from hydrogen, methyl and trifluoromethyl.

In one embodiment, $R^6$ is selected from hydrogen, methyl and trifluoromethyl, provided that when $R^6$ is selected from hydrogen and methyl, $R^4$ and $R^5$ are not both hydrogen.

In one embodiment, $R^6$ is hydrogen.

In one embodiment $R^6$ is hydrogen and $R^4$ and $R^5$ are not hydrogen.

In one embodiment $R^6$ is methyl.

In one embodiment $R^6$ is methyl and $R^4$ and $R^5$ are not both hydrogen.

In one embodiment, $R^6$ is trifluoromethyl.

In one embodiment, Y is selected from O, S, $CH_2CH_2$, $OCH_2$, and $CH_2O$.

In one embodiment, Y is O.

In one embodiment, A is a benzene ring.

In one embodiment, A is a pyridine ring.

In one embodiment Q is selected from hydrogen and $C_{1-4}$alkyl.

In one embodiment Q is selected from hydrogen and $C_{1-2}$alkyl.

In one embodiment Q is selected from hydrogen and methyl.

In one embodiment Q is hydrogen.

In one embodiment Q is methyl.

In one embodiment, the compound of formula (I) is a compound of formula (Ia):

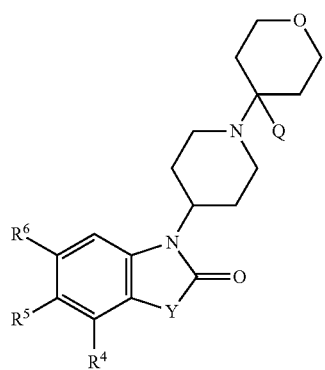

(Ia)

wherein $R^4$, $R^5$, $R^6$, Y and Q are as defined for formula (I).

In one embodiment, the compound of formula (I) is a compound of formula (Ia) wherein $R^4$ is selected from hydrogen, halogen, $C_{1-2}$alkyl, $C_{1-2}$alkyl substituted with one or more fluorine atoms, cyano, $C_{1-2}$alkylsulfonyl, $C_{1-2}$alkylsulfonyl substituted with one or more fluorine atoms, $C_{3-6}$cycloalkyl, $C_{1-2}$alkoxy, $C_{1-2}$alkoxy substituted with one or more fluorine atoms, $C_{1-2}$alkanoyl, —C(=NOC$_{1-2}$alkyl)C$_{1-2}$alkyl, $C_{1-2}$alkoxyC$_{1-2}$alkyl, and —C(O)NR$_a$R$_b$; $R^5$ is selected from hydrogen, halogen, $C_{1-2}$alkyl, $C_{1-2}$alkyl substituted with one or more fluorine atoms, cyano, $C_{1-2}$alkylsulfonyl, $C_{1-2}$alkylsulfonyl substituted with one or more fluorine atoms, $C_{3-6}$cycloalkyl, $C_{1-2}$alkoxy, $C_{1-2}$alkoxy substituted with one or more fluorine atoms, $C_{1-2}$alkanoyl, —C(=NOC$_{1-2}$alkyl)C$_{1-2}$alkyl, $C_{1-2}$alkoxyC$_{1-2}$alkyl, and —C(O)NR$_a$R$_b$; $R^6$ is selected from hydrogen, halogen, $C_{1-2}$alkyl, $C_{1-2}$alkyl substituted with one or more fluorine atoms, cyano, $C_{1-2}$alkylsulfonyl, $C_{1-2}$alkylsulfonyl substituted with one or more fluorine atoms, $C_{3-6}$cycloalkyl, $C_{1-2}$alkoxy, $C_{1-2}$alkoxy substituted with one or more fluorine atoms, $C_{1-2}$alkanoyl, —C(=NOC$_{1-2}$alkyl)C$_{1-2}$alkyl, $C_{1-2}$alkoxyC$_{1-2}$alkyl, and —C(O)NR$_a$R$_b$; Y is O; and Q is selected from hydrogen and $C_{1-2}$alkyl.

In one embodiment, the compound of formula (I) is a compound of formula (Ia) wherein $R^4$ is selected from hydrogen and fluorine, $R^5$ is selected from hydrogen and fluorine, $R^6$ is selected from hydrogen, methyl and trifluoromethyl, Y is O, and Q is selected from hydrogen and methyl.

In one embodiment, the compound of formula (I) is a compound of formula (Ia) wherein $R^4$ is selected from hydrogen and fluorine, $R^5$ is selected from hydrogen and fluorine, $R^6$ is selected from hydrogen, methyl and trifluoromethyl, Y is O, and Q is selected from hydrogen and methyl; provided that when $R^6$ is selected from hydrogen and methyl, $R^4$ and $R^5$ are not both hydrogen.

In one embodiment, there is provided a compound of formula (I) or a salt thereof wherein:
$R^4$ is selected from hydrogen and fluorine;
$R^5$ is selected from hydrogen and fluorine;
$R^6$ is selected from hydrogen, methyl and trifluoromethyl;
A is a benzene ring;
Q is selected from hydrogen and methyl; and
Y is O.

In one embodiment, there is provided a compound of formula (I) or a salt thereof wherein:
$R^4$ is selected from hydrogen and fluorine;
$R^5$ is selected from hydrogen and fluorine;
$R^6$ is selected from hydrogen, methyl and trifluoromethyl, provided that when $R^6$ is selected from hydrogen and methyl, $R^4$ and $R^5$ are not both hydrogen;
A is a benzene ring;
Q is selected from hydrogen and methyl; and
Y is O.

In one embodiment, the compound of formula (I) is a compound of formula (Ia) wherein:
$R^4$ is selected from hydrogen and fluorine;
$R^5$ is selected from hydrogen and fluorine;
$R^6$ is selected from hydrogen, methyl and trifluoromethyl;
Q is selected from hydrogen and methyl; and
Y is O.

In one embodiment, the compound of formula (I) is a compound of formula (Ia) wherein:
$R^4$ is selected from hydrogen and fluorine;
$R^5$ is selected from hydrogen and fluorine;
$R^6$ is selected from hydrogen, methyl and trifluoromethyl, provided that when $R^6$ is selected from hydrogen and methyl, $R^4$ and $R^5$ are not both hydrogen;
Q is selected from hydrogen and methyl; and
Y is O.

In one embodiment, there is provided a compound of formula (I) or a salt thereof wherein:
$R^4$ is selected from hydrogen and fluorine;
$R^5$ is selected from hydrogen and fluorine;
$R^6$ is selected from methyl and trifluoromethyl;
A is a benzene ring;
Q is selected from hydrogen and methyl; and
Y is O.

In one embodiment, there is provided a compound of formula (I) or a salt thereof wherein:
$R^4$ is selected from hydrogen and fluorine;
$R^5$ is selected from hydrogen and fluorine;
$R^6$ is selected from methyl and trifluoromethyl, provided that when $R^6$ is methyl, $R^4$ and $R^5$ are not both hydrogen;
A is a benzene ring;
Q is selected from hydrogen and methyl; and
Y is O.

In one embodiment, the compound of formula (I) is a compound of formula (Ia) wherein:
$R^4$ is selected from hydrogen and fluorine;
$R^5$ is selected from hydrogen and fluorine;
$R^6$ is selected from methyl and trifluoromethyl;
Q is selected from hydrogen and methyl; and Y is O.

In one embodiment, the compound of formula (I) is a compound of formula (Ia) wherein:
$R^4$ is selected from hydrogen and fluorine;
$R^5$ is selected from hydrogen and fluorine;
$R^6$ is selected from methyl and trifluoromethyl, provided that when $R^6$ is methyl, $R^4$ and $R^5$ are not both hydrogen;
Q is selected from hydrogen and methyl; and
Y is O.

In one embodiment, the invention provides a compound of formula (I') or a salt or solvate thereof:

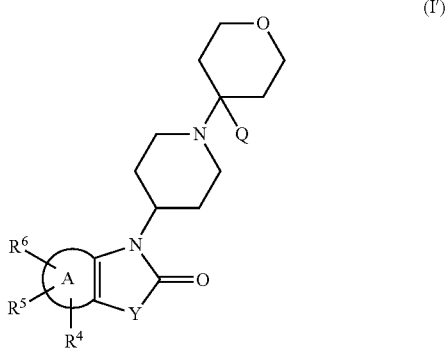

wherein:
$R^4$, $R^5$ and $R^6$ are independently selected from hydrogen, halogen, $C_{1-6}$alkyl, $C_{1-6}$alkyl substituted with one or more fluorine atoms, cyano, $C_{1-6}$alkylsulfonyl, $C_{3-6}$cycloalkyl, $C_{1-6}$alkoxy, and $C_{1-6}$alkoxy substituted with one or more fluorine atoms;
ring A is a benzene ring or 6-membered aromatic heterocylic ring containing one or two nitrogen atoms;
Q is selected from hydrogen and $C_{1-6}$alkyl; and
Y is selected from O, S, $CH_2$, CHF, $CF_2$, $CH_2CH_2$, $OCH_2$, and $CH_2O$.

It will be appreciated that the present invention covers all combinations of features and embodiments described hereinbefore.

All features and embodiments for formula (I) apply to compounds of formula (I') and (Ia) mutatis mutandis. Hereinafter, all references to compounds of formula (I) include compounds of formula (I') and (Ia).

In one embodiment the salt of the compound of formula (I) is a pharmaceutically acceptable salt. In one embodiment, the invention provides a compound of formula (I), or a pharmaceutically acceptable salt thereof.

It will be appreciated that for use in medicine the salts of compounds of formula (I) should be pharmaceutically acceptable. Suitable salts will be apparent to those skilled in the art and include for example mono- or di-basic salts formed with inorganic acids e.g. hydrochloric, hydrobromic, sulfuric, nitric, sulfamic phosphoric, hydroiodic, phosphoric or metaphosphoric acid; and with organic acids, such as tartaric, acetic, trifluoroacetic, citric, malic, lactic, fumaric, benzoic, formic, propionic, glycolic, gluconic, maleic, succinic, (1R)-(−)-10-camphorsulphonic, (1S)-(+)-10-camphorsulphonic, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example naphthalene-1,5-disulphonic, naphthalene-1,3-disulphonic, benzenesulfonic, and p-toluenesulfonic, acids. Other non-pharmaceutically acceptable salts e.g. oxalates, may be used, for example in the isolation of compounds of formula (I) and are included within the scope of this invention. Certain of the compounds of formula (I) may form acid addition salts with less than one (for example, 0.5 equivalent of a dibasic acid) or one or more equivalents of an acid. The present invention includes within its scope all possible stoichiometric and non-stoichiometric forms thereof.

The compounds of the present invention may be in the form of their free base or pharmaceutically acceptable salts thereof, particularly the hydrochloride, formate, trifluoroacetate, methanesulfonate, or 4-methylbenzenesulfonate salts.

In one embodiment, the pharmaceutically acceptable salt is a hydrochloride salt, a trifluoroacetate salt, or a formate salt.

In one embodiment the pharmaceutically acceptable salt is the hydrocholoride salt.

Solvates of the compounds of formula (I) and solvates of the salts of compounds of formula (I) are included within the scope of the present invention. As used herein, the term "solvate" refers to a complex of variable stoichiometry formed by a solute (in this invention, a compound of formula (I) or a salt thereof) and a solvent. Those skilled in the art of organic chemistry will appreciate that many organic compounds can form such complexes with solvents in which they are reacted or from which they are precipitated or crystallised. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water. Where the solvent used is water such a solvate may then also be referred to as a hydrate.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. Examples of suitable protecting groups for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Possible prodrugs for some compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

The compounds of formula (I) may have the ability to crystallise in more than one form. This is a characteristic known as polymorphism, and it is understood that such polymorphic forms ("polymorphs") are within the scope of formula (I). Polymorphism generally can occur as a response to changes in temperature or pressure or both and can also result from variations in the crystallisation process. Polymorphs can be distinguished by various physical characteristics known in the art such as x-ray diffraction patterns, solubility, and melting point.

Hereinafter, compounds of formula (I) (whether in solvated or unsolvated form) or their pharmaceutically acceptable salts (whether in solvated or unsolvated form) or prodrugs thereof defined in any aspect of the invention (except intermediate compounds in chemical processes) are referred to as "compounds of the invention".

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the invention, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples hereafter using appropriate isotopic variations of suitable reagents.

Compounds of the present invention include:—
6-Fluoro-5-methyl-3-[1-(4-methyltetrahydro-2H-pyran-4-yl)-4-piperidinyl]-1,3-benzoxazol-2(3H)-one;
6-Fluoro-3-[1-(tetrahydro-2H-pyran-4-yl)-4-piperidinyl]-1,3-benzoxazol-2(3H)-one;
3-[1-(4-Methyltetrahydro-2H-pyran-4-yl)-4-piperidinyl]-5-(trifluoromethyl)-1,3-benzoxazol-2(3H)-one; and
7-Fluoro-5-methyl-3-[1-(4-methyltetrahydro-2H-pyran-4-yl)-4-piperidinyl]-1,3-benzoxazol-2(3H)-one
and salts thereof.

In one embodiment, the compound of the present invention is selected from:—
6-Fluoro-5-methyl-3-[1-(4-methyltetrahydro-2H-pyran-4-yl)-4-piperidinyl]-1,3-benzoxazol-2(3H)-one;
3-[1-(4-Methyltetrahydro-2H-pyran-4-yl)-4-piperidinyl]-5-(trifluoromethyl)-1,3-benzoxazol-2(3H)-one; and
7-Fluoro-5-methyl-3-[1-(4-methyltetrahydro-2H-pyran-4-yl)-4-piperidinyl]-1,3-benzoxazol-2(3H)-one
and salts thereof.

In one embodiment, the salt of a compound listed above is a pharmaceutically acceptable salt. In one embodiment, the salt is a hydrochloride salt, trifluoroacetate salt or a formate salt.

In one embodiment, the salt is a hydrochloride salt.

In one embodiment, the compound of the present invention is selected from:—
6-Fluoro-5-methyl-3-[1-(4-methyltetrahydro-2H-pyran-4-yl)-4-piperidinyl]-1,3-benzoxazol-2(3H)-one hydrochloride;
6-Fluoro-3-[1-(tetrahydro-2H-pyran-4-yl)-4-piperidinyl]-1,3-benzoxazol-2(3H)-one hydrochloride;
3-[1-(4-Methyltetrahydro-2H-pyran-4-yl)-4-piperidinyl]-5-(trifluoromethyl)-1,3-benzoxazol-2(3H)-one hydrochloride; and
7-Fluoro-5-methyl-3-[1-(4-methyltetrahydro-2H-pyran-4-yl)-4-piperidinyl]-1,3-benzoxazol-2(3H)-one hydrochloride.

In one embodiment, the compound of the present invention is selected from:—
6-Fluoro-5-methyl-3-[1-(4-methyltetrahydro-2H-pyran-4-yl)-4-piperidinyl]-1,3-benzoxazol-2(3H)-one hydrochloride;
3-[1-(4-Methyltetrahydro-2H-pyran-4-yl)-4-piperidinyl]-5-(trifluoromethyl)-1,3-benzoxazol-2(3H)-one hydrochloride; and
7-Fluoro-5-methyl-3-[1-(4-methyltetrahydro-2H-pyran-4-yl)-4-piperidinyl]-1,3-benzoxazol-2(3H)-one hydrochloride.

In a further aspect, the invention provides a general process (A1) for preparing compounds of formula (I) in which Q=H, which process comprises:
coupling a compound of formula (II):

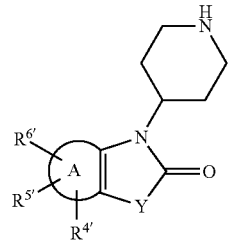

with a compound of formula (III)

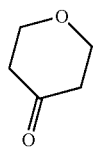

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, and Y is O, S, CH$_2$ optionally substituted with one or two fluorine atoms, CH$_2$ optionally substituted with one or two methyl groups, CH$_2$CH$_2$, OCH$_2$, or CH$_2$O.

The reaction is carried out under conditions suitable for reductive alkylation. The reductive alkylation reaction is typically carried out using sodium triacetoxyborohydride in dichloroethane, optionally in the presence of triethylamine, and optionally in the presence of titanium tetraisopropoxide. Alternatively sodium cyanoborohydride can be used as the reducing reagent in solvents such as methanol or ethanol, or the reductive alkylation can be effected under catalytic hydrogenation conditions using a palladium catalyst. In a further variation, the compounds (II) and (III) can be condensed under dehydrating conditions e.g. molecular sieves or magnesium sulfate, and the resultant imine or enamine reduced using for example sodium borohydride or by catalytic hydrogenation.

A modification of general process (A1) is required where Q is $C_{1-6}$alkyl. Thus, in general process (A2), a compound of formula (II) can be reacted with a compound of formula (III) in the presence of a source of cyanide, e.g. acetone cyanohydrin, to form the cyano intermediate (IV) which can be reacted with an alkyl Grignard reagent QMgX to form compounds of formula (I) in which Q is $C_{1-6}$alkyl.

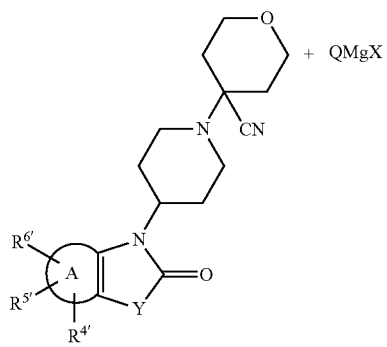
(IV)

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y is O, S, $CH_2$ optionally substituted with one or two fluorine atoms, $CH_2$ optionally substituted with one or two methyl groups, $CH_2CH_2$, $OCH_2$, or $CH_2O$, Q is $C_{1-6}$alkyl, and X is bromo or iodo or chloro.

In a further aspect, the invention provides a general process (B) for preparing compounds of formula (I) in which Y=O or S, which process comprises:
coupling a compound of formula (V)

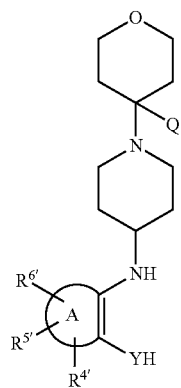
(V)

with a compound of formula (VI)

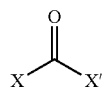
(VI)

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y is O or S, Q is as previously defined, and X and X' both represent leaving groups. X and X' can be the same or different and examples are Cl, PhO, EtO, imidazole. When X and X' are both Cl, i.e. phosgene, this reagent can be generated in situ e.g. from diphosgene or triphosgene.

The above reaction is carried out using standard methodology e.g. reacting the amine (V) with the reagent (VI) in an inert solvent for example dichloromethane or toluene, optionally in the presence of a base such as triethylamine or potassium carbonate, and optionally with heating.

In a further aspect, the invention provides a general process (C) for preparing compounds of formula (I) in which Y=$CH_2$, which process comprises:
hydrolysis, decarboxylation and cyclisation of compound of formula (VII), using conditions similar to those published in Tet Lett 2001, 42, 6943

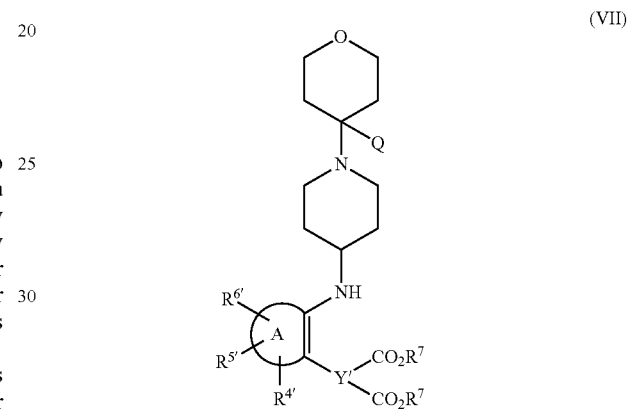
(VII)

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y' is CH, Q is as previously defined, and $R^7$ represents $C_{1-6}$alkyl, benzyl, or other acid protecting group.

In a further aspect, the invention provides a general process (D) for preparing compounds of formula (I) in which Y=$CH_2CH_2$, which process comprises:
hydrolysis and cyclisation of a compound of formula (VIII)

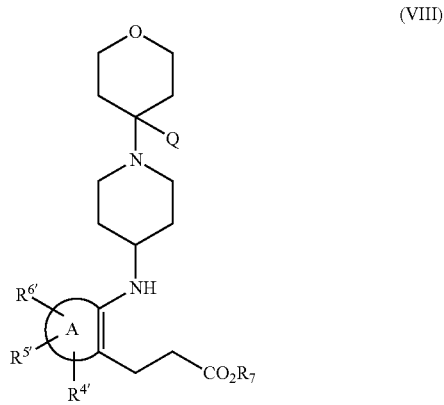
(VIII)

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Q is as previously defined, and $R_7$ represents $C_{1-6}$ alkyl, benzyl, or other acid protecting group. Hydrolysis of the ester $CO_2R_7$ group can be accomplished using standard conditions, and cyclisation can be effected by activation of the acid group using for example EDC (1-ethyl-3-(dimethylaminopropyl)carbodiimide) and HOBT (hydroxybenzotriazole).

In a further aspect, the invention provides a general process (E) for preparing compounds of formula (I) in which $Y=OCH_2$, which process comprises:
treatment of a compound of formula (IX) with a base, such as $KO^tBu$ in an inert solvent for example THF, optionally with heating.

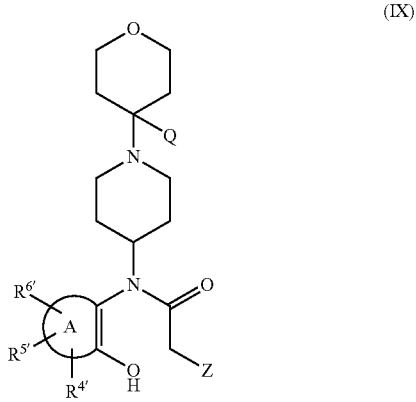

(IX)

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Q is as previously defined, and Z is a leaving group such as bromo or chloro.

In a further aspect, the invention provides a general process (F) for preparing compounds of formula (I) which process comprises:
treatment of a compound of formula (X)

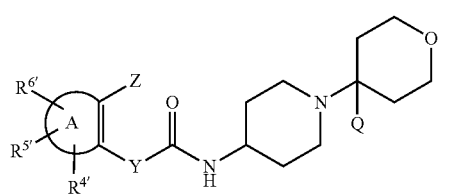

(X)

with a palladium or copper catalyst (XII) to effect an intramolecular cyclisation; wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y is O, S, $CH_2$ optionally substituted with one or two fluorine atoms, $CH_2$ optionally substituted with one or two methyl groups, $CH_2CH_2$, $OCH_2$, or $CH_2O$, Q is as previously defined, and Z is a leaving group such as bromo, iodo, chloro or triflate.

The cyclisation reaction can be carried out using a variety of palladium or copper reagents as described in the literature (JACS, 2003, 125, 6653; Tet. Lett., 2004, 45, 8535; or JACS, 2002, 124, 7421.)

In a further aspect, the invention provides a general process (G) for preparing compounds of formula (I) which process comprises:
coupling a compound of formula (XIII):

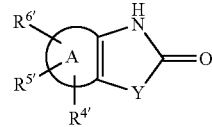

(XIII)

with a compound of formula (XIV)

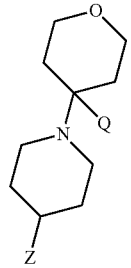

(XIV)

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y is O, S, $CH_2$ optionally substituted with one or two fluorine atoms, $CH_2$ optionally substituted with one or two methyl groups, $CH_2CH_2$, $OCH_2$, or $CH_2O$, Q is as previously defined, and Z is hydroxy or a leaving group such as chloro, bromo or iodo, or alkyl/aryl sulfonate.

The alkylation reaction can be carried out under classical alkylation (Z=a leaving group) or Mitsunobu reaction (Z=OH) conditions. Using classical alkylation conditions, the intermediate (XIII) can be deprotonated using a base such as sodium hydride in an inert solvent such as dimethylformamide, and then treated with the alkylating reagent (XIV), optionally with heating. The Mitsunobu reaction with (XIII) and (XIV) Z=OH can be carried out using standard conditions e.g. triphenylphosphine and diethylazodicarboxylate in an inert solvent such as dichloromethane or tetrahydrofuran at room temperature.

Conversion of $R^{6'}$, $R^{5'}$ and $R^{4'}$ to $R^6$, $R^5$ and $R^4$ respectively, or interconversions of $R^6$, $R^5$ and $R^4$ may be accomplished as illustrated below for $R^{6'}$.

For example, when $R^{6'}$ is a halogen, it can be converted to an alkoxy, trifluoromethyl or methylsulphonyl group by copper catalysed reaction, using an alcohol, methyl fluorosulfonyl(difluoro)acetate or sodium methanesulphinate respectively. It may also be converted to an alkyl group with an organometallic reagent, for example an alkylstannane.

Alternatively, when $R^{6'}$ is a halogen, it can also be converted to a cyano group, for example, by palladium catalysed reaction using zinc cyanide.

As another example, when $R^{6'}$ is hydroxy, it may be converted to alkoxy by reaction with an alkyl halide or sulfonate, or to trifluoromethoxy by conversion to the xanthate followed by oxidation in the presence of fluoride ion.

As a further example, when $R^{6'}$ is methyl, it may be converted to trifluoromethyl by chlorination or bromination followed by displacement of the introduced halogens with fluoride.

Conversion of compounds wherein $Y=CH_2$ to compounds wherein $Y=C(Me)_2$ can be achieved by treatment of the $Y=CH_2$ compound with strong base e.g. sodium hydride in an inert solvent e.g. DMF, followed by addition of excess methyl iodide.

Compounds of formula (II) are generally known in the literature or can be prepared by a range of different processes for example:

(a) reductive amination of the amine (XV) with the ketone (XVI), wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y' is a group OH or SH or a group convertible to Y', and P represents a nitrogen protecting group e.g. Boc, acetyl, trifluoroacetyl, ethoxycarbonyl, benzyloxycarbonyl, to give (XVII), followed by deprotection of Y' if necessary, and cyclisation using phosgene or a phosgene equivalent, and deprotection of the piperidine nitrogen using standard literature conditions (Scheme 1).

Scheme 1.

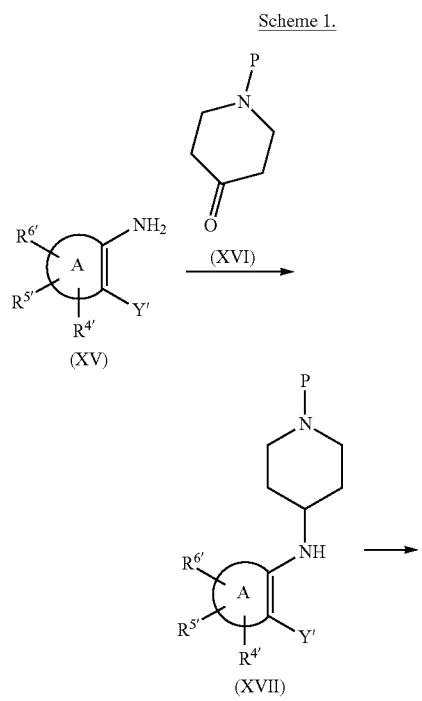

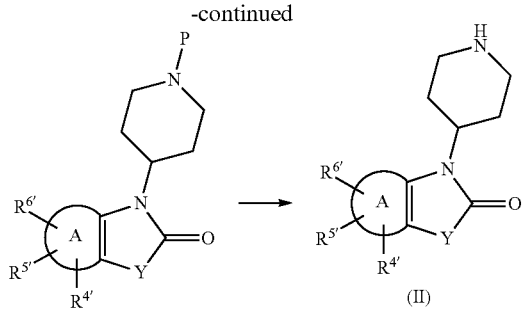

Compounds of formula (XV) are commercially available or can be prepared by standard methodology. The compound (XVI) in which P=Boc is commercially available (b) metal catalysed cyclisation of an intermediate (XVIII) followed by deprotection of the piperidine nitrogen, wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y is O, S, $CH_2$ optionally substituted with one or two fluorine atoms, $CH_2CH_2$, $OCH_2$, or $CH_2O$, P represents a nitrogen protecting group (e.g. Boc, acetyl, trifluoroacetyl, benzyloxycarbonyl), and Z represents a leaving group such as bromo, iodo, chloro or triflate. Reaction conditions for the metal catalysed cyclisation are summarised in Process F. The carbamate, thiocarbamate or amide (XVIII) can be prepared using any of the classical methods for formation of this functionality as illustrated in Scheme 2. Compounds of formula (XIX) and (XI) are commercially available or can be prepared by known methodology. The compound (XX) in which P=Boc is commercially available. The compound (LX) can be prepared from N-protected piperidine-4-carboxylic acid, for example by Curtius rearrangement using diphenylphosphoryl azide.

Scheme 2.

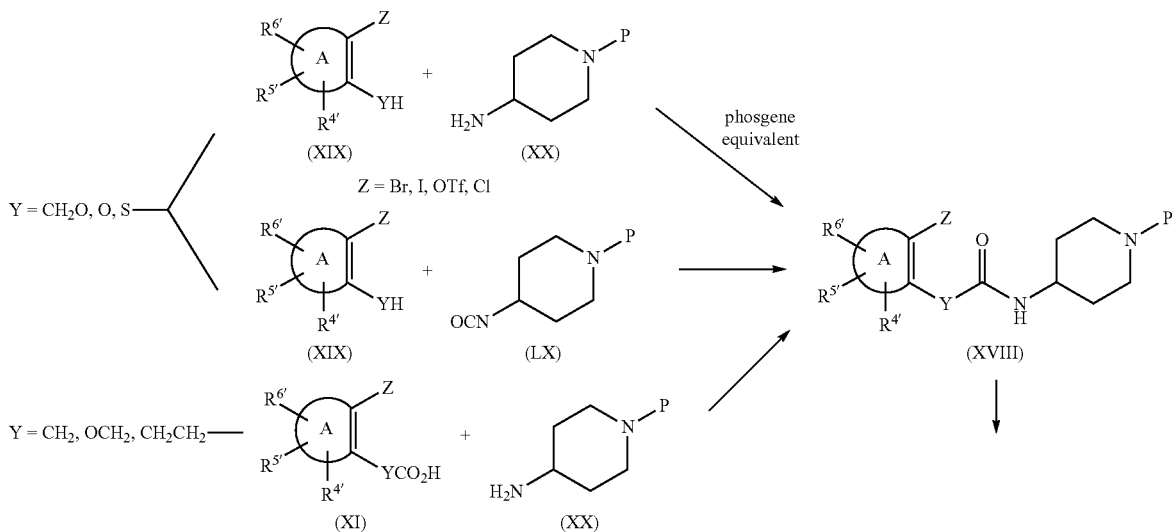

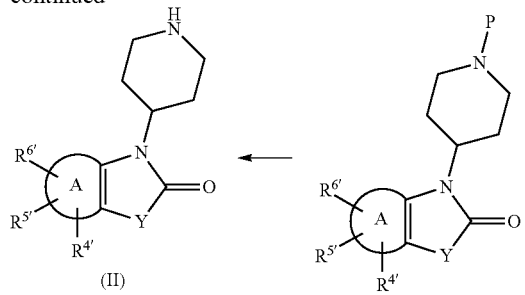

(II)

(c) metal catalysed reaction between the amine (XX) and a suitably substituted aromatic compound (XXI) wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y' is OH or SH or a group convertible to Y', P represents a nitrogen protecting group (e.g. Boc, acetyl, trifluoroacetyl, benzyloxycarbonyl), and Z represents a leaving group such as bromo, iodo, chloro or triflate (Scheme 3). This process generates intermediates of formula (XXII) and subsequent reactions are similar to that for Scheme 1. Compounds of formula (XXI) are commercially available or can be prepared by known methodology. The compound (XX) in which P=Boc is commercially available with one or two fluorine atoms, $CH_2CH_2$, $OCH_2$, or $CH_2O$, P represents a nitrogen protecting group (e.g. Boc, acetyl, trifluoroacetyl, benzyloxycarbonyl), and Z represents a leaving group such as bromo, iodo, chloro, or mesylate, to give the intermediate (XXIV), followed by deprotection of the piperidine nitrogen (Scheme 4). Compounds of formula (XIII) are commercially available or can be prepared by known methodology.

Scheme 4.

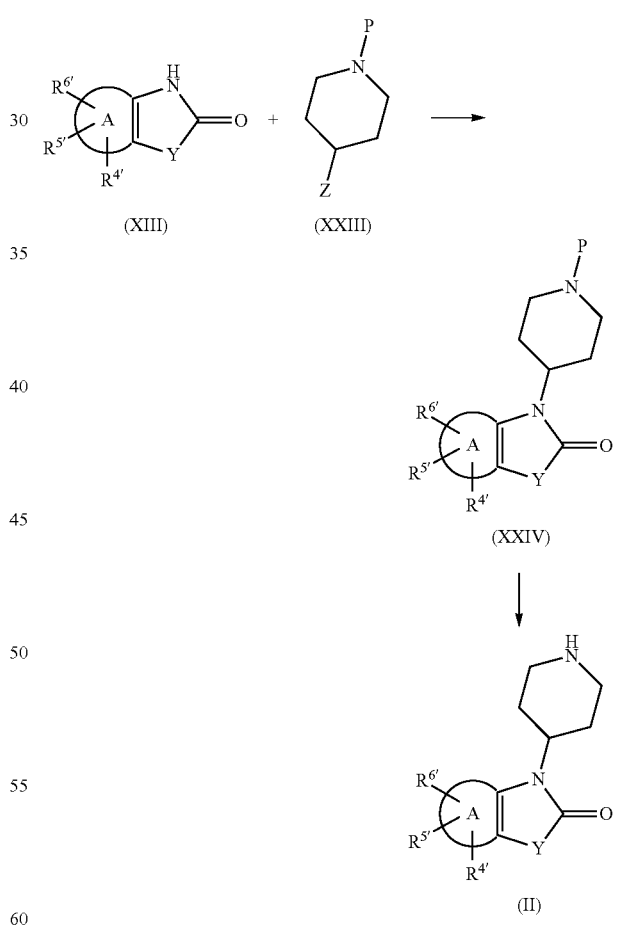

Scheme 3.

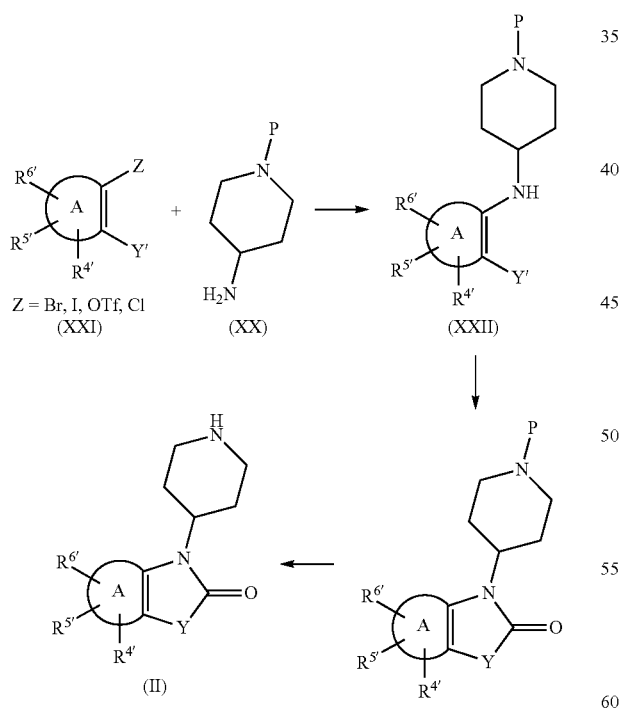

(d) alkylation of the heterocycle (XIII) with the intermediate (XXIII) wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y is O, S, $CH_2$ optionally substituted Compounds of formula (III) can be prepared by standard literature methodology.

Compounds of formula (V) can be prepared by a number of different processes e.g.

(e) metal catalysed reaction of the amine (XXV) with the ortho substituted aromatic compound (XXI), wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y' is OH or SH or a group convertible to Y', Q is as previously defined, and Z represents a leaving group such as bromo, iodo, chloro or triflate (Scheme 5). Compounds of formula (XXI) are commercially available or can be prepared by standard methodology. Compounds of formula (XXV) can be prepared as shown in Schemes 12 and 13.

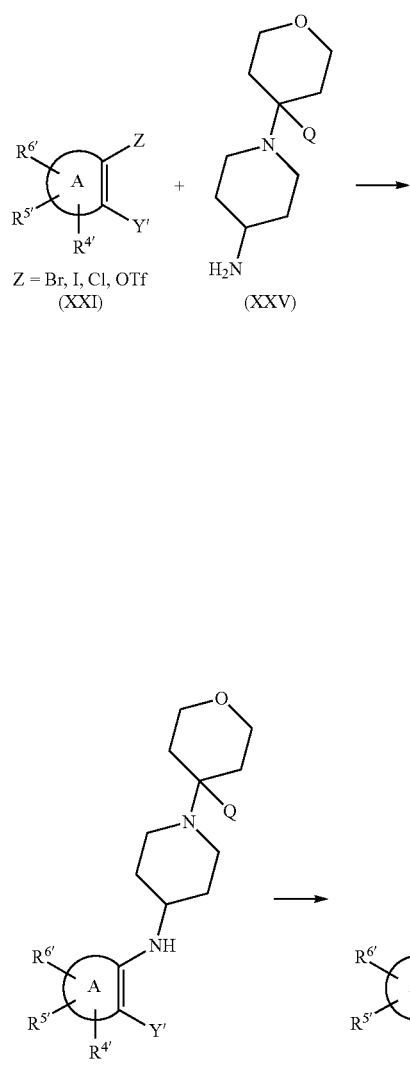

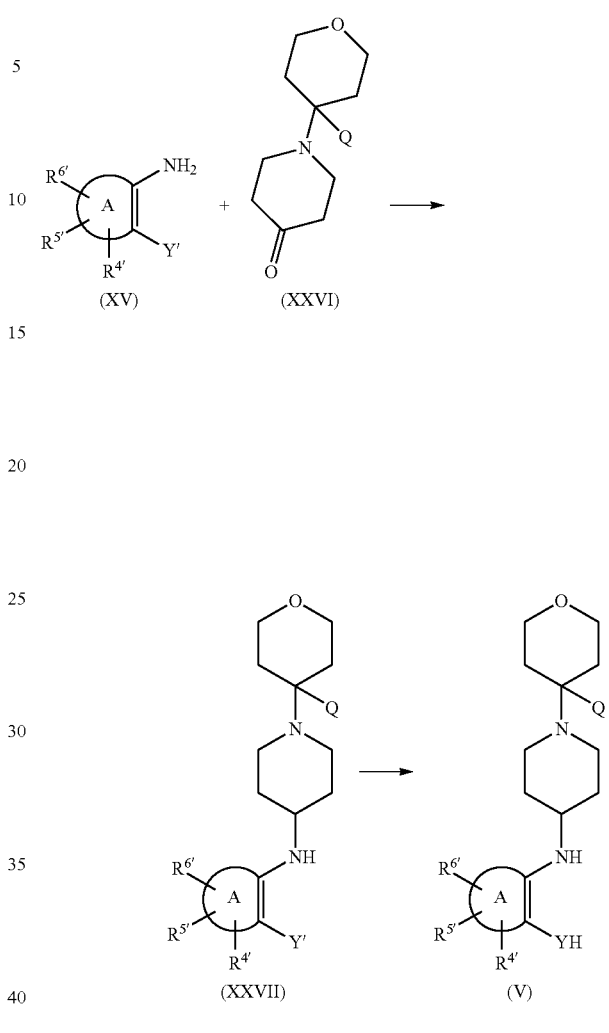

(f) Reductive alkylation of the amine (XV) with the piperidone (XXVI) wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y' is OH or SH or a group convertible to Y' and Q is as previously defined, using for example sodium triacetoxyborohydride in dichloroethane to give the intermediate (XXVII), followed by deprotection of Y' if required (Scheme 6). Compounds of formula (XXVI) can be prepared as shown in Schemes 13 and 14.

Compounds of formula (VI) are commercially available e.g. carbonyl diimidazole, phosgene, diphosgene, triphosgene, phenyl chloroformate, diethyl carbonate.

Compounds of formula (VII) in which Y' is CH can be prepared as illustrated in Scheme 7.

Displacement of Z from the substituted nitro compound (XXVIII) with the malonate (XXIX) wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Q is as previously defined, and $R^7$ is an $C_{1-6}$alkyl or arylalkyl group, using standard conditions for aromatic nucleophilic substitution (Scheme 7) to give (XXX), followed by reduction of the nitro group, and reductive alkylation of the resultant aniline (XXXI) with the ketone (XXVI). Compounds of formula (XXVIII) are commercially available, or can be prepared using standard literature methodology. Compounds of formula (XXIX) are commercially available.

Scheme 7.

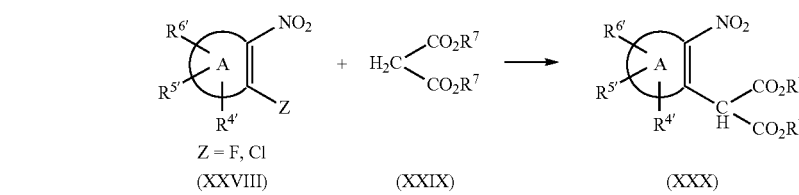

(XXVIII)   (XXIX)   (XXX)

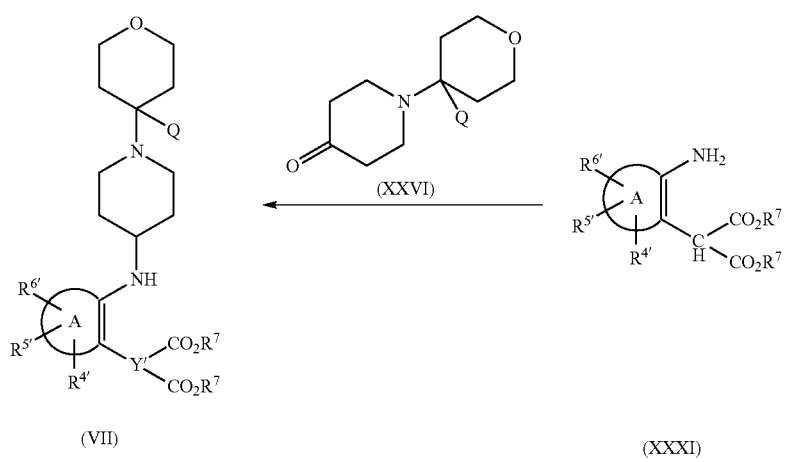

(VII)   (XXXI)

Compounds of formula (VIII) can be prepared as illustrated in Scheme 8.

Wittig-Horner reaction of the aldehyde (XXXII) with the appropriate phosphono acetate (XXXIIb) provides the cinnamate (XXXIII). Reduction of the nitro group and double bond leading to the aniline (XXXIV), can be followed by reductive alkylation to give (VIII) (Scheme 8), wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Q is as previously defined, and $R^7$ is a $C_{1-6}$alkyl group or other acid protecting group. Compounds of formula (XXXII) are commercially available, or can be prepared using standard literature methodology. Compounds of formula (XXXIIb) are commercially available.

Scheme 8.

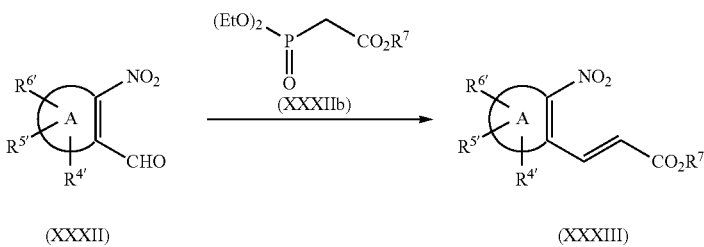

(XXXII)   (XXXIII)

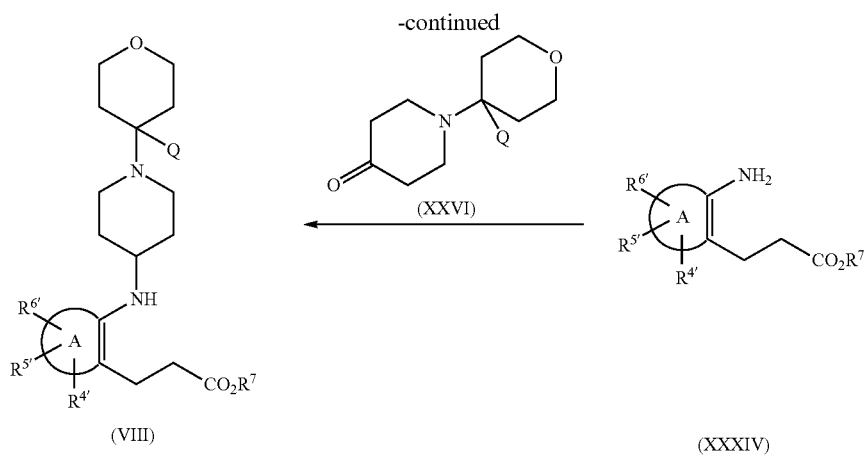

(VIII)    (XXXIV)

Compounds of formula (IX) can be prepared as illustrated in Scheme 9.

Reductive alkylation of the amine (XXXV) with the ketone (XXVI) provides the intermediate (XXXVI), which can then be acylated with the appropriate acid chloride, using standard alkylation conditions to give (IX), wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Q is as previously defined, and Z is a leaving group such as chloro or bromo. Compounds of formula (XXXV) are commercially available, or can be prepared by reduction of the respective commercially available nitro-compound.

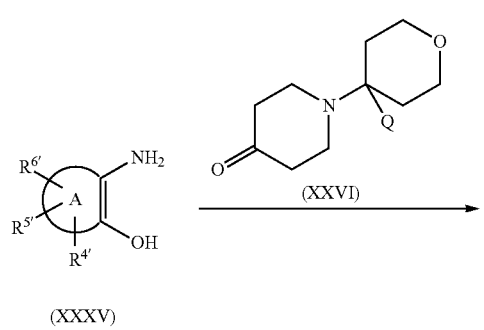

Scheme 9.

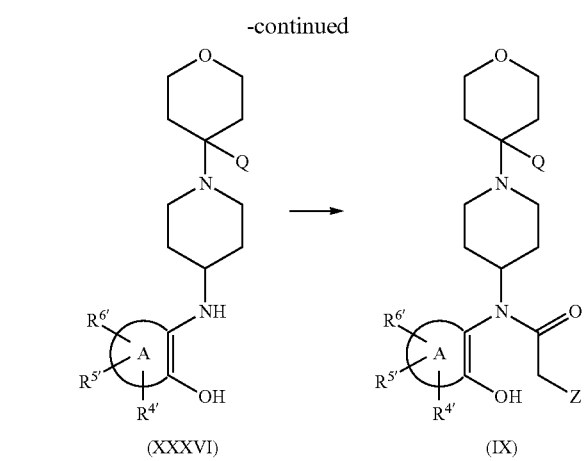

(XXXVI)    (IX)

Compounds of formula (X) can be prepared by a variety of processes e.g. as illustrated in Scheme 10 by:
  combining the alcohol/thiol (XIX) and the amine (XXV) with phosgene or a phosgene equivalent using standard conditions. Phosgene equivalents include carbonyl diimidazole, diphosgene, triphosgene, phenyl chloroformate;
  reacting the alcohol/thiol (XIX) with the isocyanate (XXXVII).
  wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously described, Y is O or S, Z is a leaving group such as bromo, iodo, chloro or triflate, and Q is as previously defined.

The isocyanate (XXXVII) can be prepared from the corresponding amine (XXV) using standard methodology for isocyanate formation.

Scheme 10.

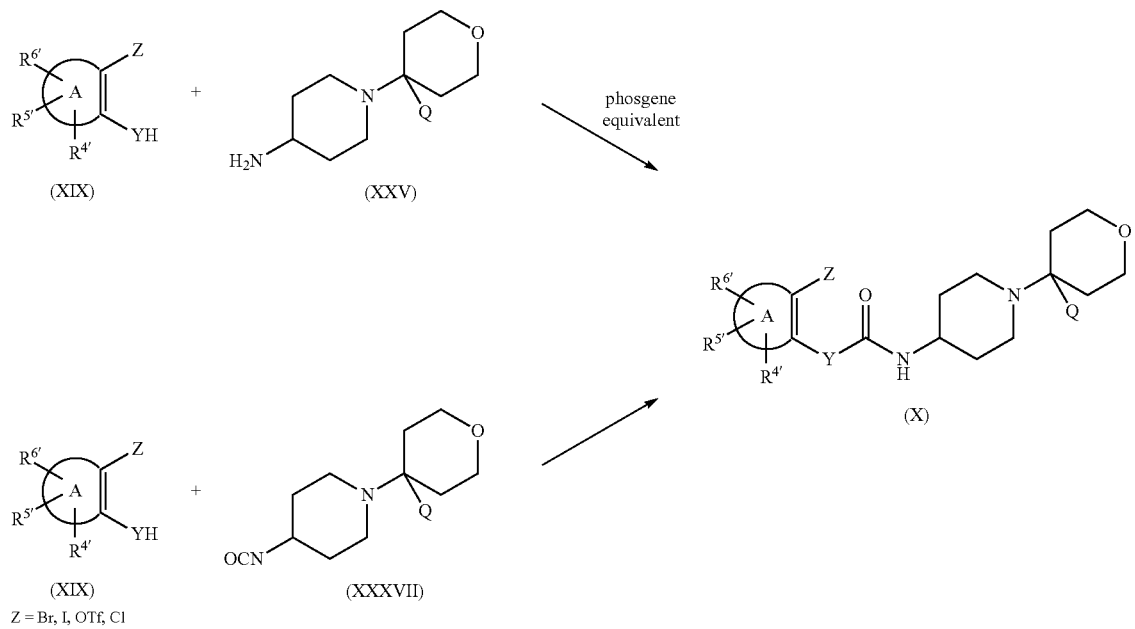

Z = Br, I, OTf, Cl

Palladium and copper catalysts (XII) are commercially available or can be prepared as described in the literature (see references in Process F).

Compounds of formula (XIII) are commercially available or can be prepared by literature processes.

Compounds of formula (XIV) where Q=H can be prepared as shown in Scheme 11, by reductive alkylation of (XXXVIII) where Z' represents Z or a group convertible to Z with the ketone (III). Compounds of formula (XXXVIII) in which Z' is OH can be prepared by reduction of an N-protected piperidone, followed by deprotection. Conversion of a Z' hydroxy group to Z=chloro or bromo can be accomplished using standard methodology e.g. treatment with thionyl chloride or triphenylphosphine/carbon tetrabromide.

Scheme 11.

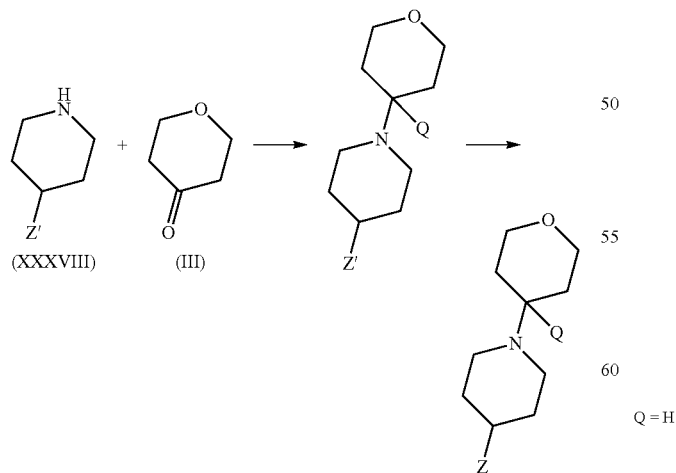

Q = H

The compound (XXV) where Q=H can be prepared as shown in Scheme 12. Reductive alkylation of the commercially available amine (XXXIX) with the cyclohexanone (III) using for example sodium triacetoxyborohydride in dichloroethane provides the intermediate (XL) which is deprotected using HCl in ethanol or trifluoroacetic acid to afford the primary amine (XXV).

Scheme 12.

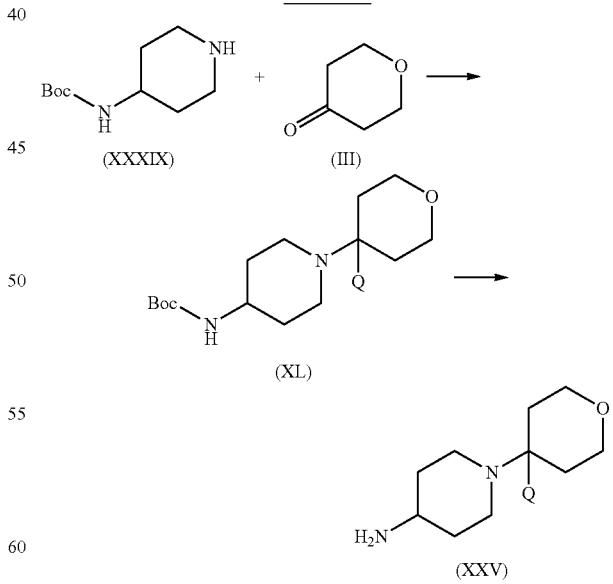

The compound (XXV) where Q=alkyl can be prepared from intermediates (XXXIX) and (III) using similar methodology as in process A2, followed by deprotection.

Alternatively the compounds (XXV) and (XXVI) where Q=H can be prepared as shown in Scheme 13. Reductive amination of cyclohexanone (III) using for example ammonia solution under catalytic hydrogenation conditions provides intermediate amine (XLI), which can be converted into piperidinone (XXVI) by reaction with quaternary piperidine salt (XLII). Reductive amination, for example using ammonia and catalytic hydrogenation, affords primary amine (XXV).

Scheme 13.

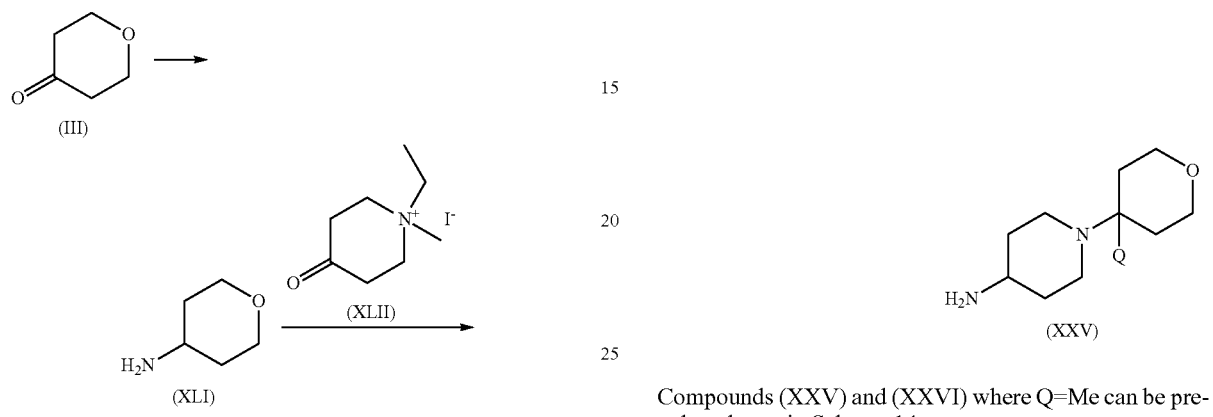

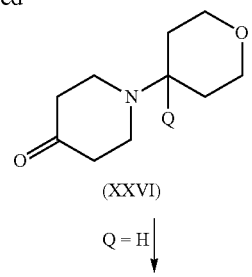

Compounds (XXV) and (XXVI) where Q=Me can be prepared as shown in Scheme 14.

Scheme 14.

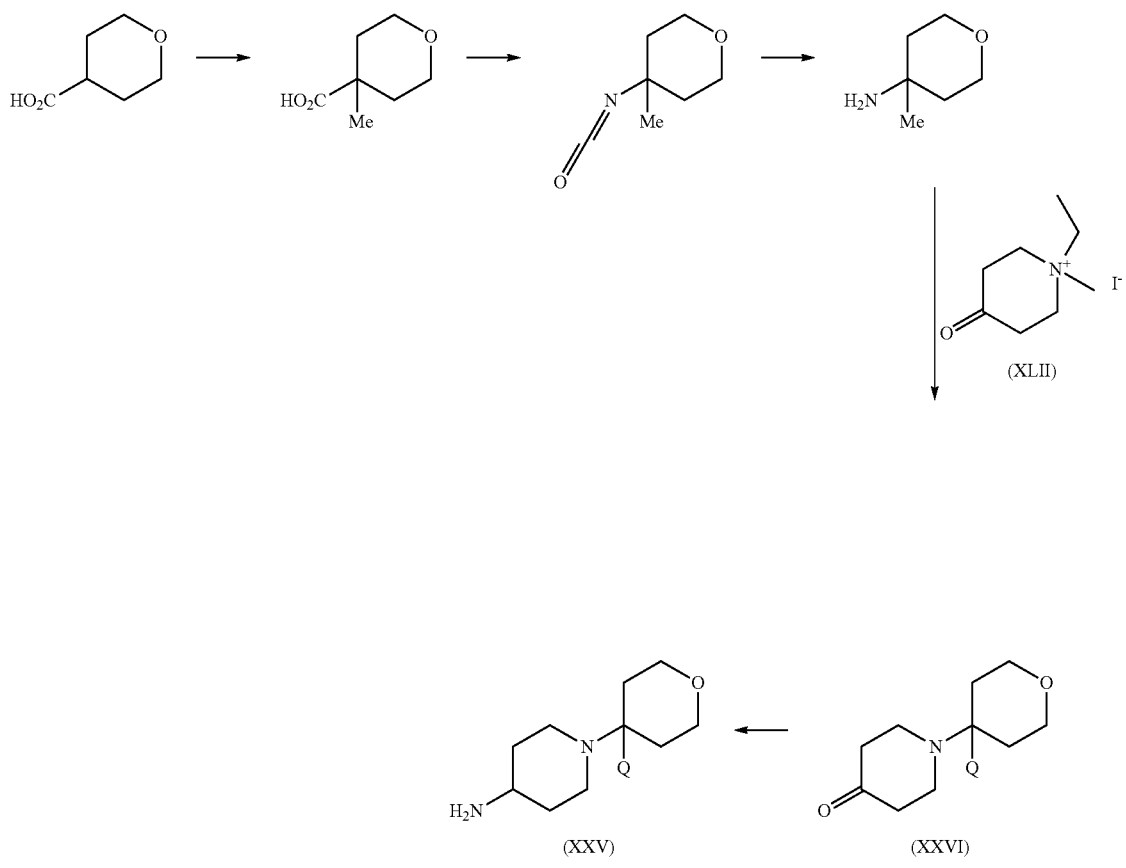

Q = Me

Compounds of the present invention are $M_1$ receptor agonists. Selective $M_1$ receptor agonists are said to be useful to ameliorate positive and cognitive symptoms of psychotic disorders such as schizophrenia, schizo-affective disorders, schizophreniform diseases, psychotic depression, mania, acute mania, paranoid and delusional disorders, and cognitive impairment including memory disorders such as Alzheimer's disease without peripheral cholinergic side effects mediated predominantly through $M_2$ and $M_3$ receptors. $M_1$ receptor agonists may also be suitable for combination with other typical and atypical antipsychotics and other actives such as mood stabilisers, antidepressants, anxiolytics, drugs for extrapyramidal side effects and cognitive enhancers, to provide improved treatment of psychotic disorders.

$M_1$ receptor agonists may also be suitable for treatment of the underlying pathology associated with Alzheimer's Disease, or in a preventative role.

Thus in a further aspect, the invention provides a compound of formula (I) as hereinbefore described or a pharmaceutically acceptable salt thereof for use in therapy.

In another aspect, the invention provides a compound of formula (I) or a pharmaceutically acceptable salt thereof for use in the treatment of a condition wherein agonism of a muscarinic $M_1$ receptor would be beneficial.

The terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). Treatment of the various subtypes of the disorders mentioned herein is contemplated as part of the present invention. Numbers in brackets after the listed diseases below refer to the classification code in DSM-IV.

Within the context of the present invention, the term psychotic disorder includes Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9);

Other conditions wherein agonism of the $M_1$ receptor would be beneficial in their treatment include:

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90);

Anxiety disorders including Social Anxiety Disorder, Panic Attack, Agoraphobia, Panic Disorder, Agoraphobia Without History of Panic Disorder (300.22), Specific Phobia (300.29) including the subtypes Animal Type, Natural Environment Type, Blood-Injection-Injury Type, Situational Type and Other Type), Social Phobia (300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder and Anxiety Disorder Not Otherwise Specified (300.00);

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide;

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition; and Substance-Induced Sleep Disorder including the subtypes Insomnia Type, Hypersomnia Type, Parasomnia Type and Mixed Type;

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; and Eating Disorder Not Otherwise Specified (307.50);

Autistic Disorder (299.00); Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23);

Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9);

Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9); and Alzheimer's Type Dementia including Dementia of the Alzheimer's Type, With Early Onset, Without Behavioural Disturbance (294.10); Dementia of the Alzheimer's Type, With Late Onset, Without Behavioural Disturbance (294.10); Dementia of the Alzheimer's Type, With Early Onset, With Behavioural Disturbance (294.11); Dementia of the Alzheimer's Type, With Late Onset, With Behavioural Disturbance (294.11).

The compounds of formula (I) may also be useful for the enhancement of cognition, including both the treatment of cognitive impairment on its own and the treatment of cognition impairment in other diseases such as schizophrenia, bipolar disorder, depression, other psychiatric disorders and psychotic conditions associated with cognitive impairment. Where cognitive impairment results from a treatment of a disease, $M_1$ agonists may be beneficial. For example, when the treatment of epilepsy with anticonvulsants results in cognitive impairment, an $M_1$ agonist may be useful for the alleviation or treatment of the cognitive impairment.

Within the context of the present invention, the term cognitive impairment includes, for example, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to psychosis, and post-electroconvulsive treatment related cognitive disorders; and dyskinetic disorders such as Parkinson's disease, neuroleptic-induced parkinsonism, and tardive dyskinesias.

Compounds of formula (I) or pharmaceutically acceptable salts thereof may also be used as memory and/or cognition enhancers in healthy humans with no cognitive and/or memory deficit.

In another aspect, the invention provides a compound of formula (I) as hereinbefore described or a pharmaceutically acceptable salt thereof for use in the treatment of a psychotic disorder. In one embodiment, the invention provides a compound of formula (I) as hereinbefore described or a pharmaceutically acceptable salt thereof for use in the treatment of schizophrenia.

The invention also provides a compound of formula (I) as hereinbefore described or a pharmaceutically acceptable salt thereof for use in the treatment of cognitive impairment.

The invention also provides a compound of formula (I) as hereinbefore described or a pharmaceutically acceptable salt thereof for use in the treatment of Alzheimer's Disease.

In another aspect, the invention provides the use of a compound of formula (I) as hereinbefore described or a pharmaceutically acceptable salt thereof in the manufacture of a medicament for the treatment of a condition wherein agonism of the $M_1$ receptor would be beneficial.

In another aspect, the invention provides the use of a compound of formula (I) as hereinbefore described or a pharmaceutically acceptable salt thereof in the manufacture of a medicament for the treatment of a psychotic disorder. In one embodiment, the invention provides the use of a compound of formula (I) as hereinbefore described or a pharmaceutically acceptable salt thereof in the manufacture of a medicament for the treatment of schizophrenia.

In another aspect, the invention provides a compound of formula (I) as hereinbefore described or a pharmaceutically acceptable salt thereof for the treatment of a psychotic disorder. In one embodiment, the invention provides a compound of formula (I) as hereinbefore described or a pharmaceutically acceptable salt thereof for the treatment of schizophrenia.

The invention also provides the use of a compound of formula (I) as hereinbefore described or a pharmaceutically acceptable salt thereof in the manufacture of a medicament for the treatment of cognitive impairment.

The invention also provides a compound of formula (I) as hereinbefore described or a pharmaceutically acceptable salt thereof for the treatment of cognitive impairment.

The invention also provides the use of a compound of formula (I) as hereinbefore described or a pharmaceutically acceptable salt thereof in the manufacture of a medicament for the treatment of Alzheimer's Disease.

The invention also provides a compound of formula (I) as hereinbefore described or a pharmaceutically acceptable salt thereof for the treatment of Alzheimer's Disease.

In another aspect, the invention provides a method of treating a condition where agonism of the $M_1$ receptor would be beneficial, which comprises administering to a mammal in need thereof an effective amount of a compound of formula (I) as hereinbefore described or a pharmaceutically acceptable salt thereof. In one embodiment, the mammal is a human.

In another aspect, the invention provides a method of treating a psychotic disorder which comprises administering to a mammal in need thereof an effective amount of a compound of formula (I) as hereinbefore described or a pharmaceutically acceptable salt thereof. In one embodiment, the invention provides a method of treating schizophrenia, which comprises administering to a mammal in need thereof an effective amount of a compound of formula (I) as hereinbefore described or a pharmaceutically acceptable salt thereof. In one embodiment, the mammal is a human.

The invention also provides a method of treating cognitive impairment, which comprises administering to a mammal in need thereof an effective amount of a compound of formula (I) as hereinbefore described or a pharmaceutically acceptable salt thereof. In one embodiment, the mammal is a human.

The invention also provides a method of treating Alzheimer's Disease, which comprises administering to a mammal in need thereof an effective amount of a compound of formula (I) as hereinbefore described or a pharmaceutically acceptable salt thereof. In one embodiment, the mammal is a human.

The compounds of formula (I) and pharmaceutically acceptable salts thereof may also be suitable for combination with other actives, such as typical and atypical antipsychotics, mood stabilisers, antidepressants, anxiolytics, drugs for extrapyramidal side effects and cognitive enhancers to provide improved treatment of psychotic disorders.

The combination therapies of the invention are, for example, administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) or a pharmaceutically acceptable salt thereof and at least one antipsychotic agent, a mood stabiliser, an antidepressant, an anxiolytic, a drug for extrapyramidal side effects or a cognitive enhancer are within the scope of the current invention. In one embodiment of adjunctive therapeutic administration as described herein, a patient is typically stabilised on a therapeutic administration of one or more of the components for a period of time and then receives administration of another component. The compounds of formula (I) or a pharmaceutically acceptable salt thereof may be administered as adjunctive therapeutic treatment to patients who are receiving administration of at least one antipsychotic agent, a mood stabiliser, an antidepressant, an anxiolytic, a drug for extrapyramidal side effects or a cognitive enhancer, but the scope of the invention also includes the adjunctive therapeutic administration of at least one antipsychotic agent, a mood stabiliser, an antidepressant, an anxiolytic, a drug for extrapyramidal side effects or a cognitive enhancer to patients who are receiving administration of compounds of formula (I) or a pharmaceutically acceptable salt thereof.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect therefore, the invention provides a method of treatment of a psychotic disorder by adjunctive therapeutic administration of compounds of formula (I) or a pharmaceutically acceptable salt thereof to a patient receiving therapeutic administration of at least one antipsychotic agent. In a further aspect, the invention provides the use of compounds of formula (I) or a pharmaceutically acceptable salt thereof in the manufacture of a medicament for adjunctive therapeutic administration for the treatment of a psychotic disorder in a patient receiving therapeutic administration of at least one antipsychotic agent. In a further aspect, the invention provides compounds of formula (I) or a pharmaceutically acceptable salt thereof for adjunctive therapeutic administration for the treatment of a psychotic disorder in a patient receiving therapeutic administration of at least one antipsychotic agent. The invention further provides compounds of formula (I) or a pharmaceutically acceptable salt thereof for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I) or a pharmaceutically acceptable salt thereof. In a further aspect, the invention provides the use of at least one antipsychotic agent in the manufacture of a medicament for adjunctive therapeutic administration for the treatment of a psychotic disorder in a patient receiving therapeutic administration of compounds of formula (I) or a pharmaceutically acceptable salt thereof. In a further aspect, the invention provides at least one antipsychotic agent for adjunctive therapeutic administration for the treatment of a psychotic disorder in a patient receiving therapeutic administration of compounds of formula (I) or a pharmaceutically acceptable salt thereof. The invention further provides at least one antipsychotic agent for adjunctive therapeutic administration for the treatment of a psychotic disorder in a patient receiving therapeutic administration of compounds of formula (I) or a pharmaceutically acceptable salt thereof.

In a further aspect, the invention provides a method of treatment of a psychotic disorder by simultaneous therapeutic administration of compounds of formula (I) or a pharmaceutically acceptable salt thereof in combination with at least one antipsychotic agent. The invention further provides the use of a combination of compounds of formula (I) or a pharmaceutically acceptable salt thereof and at least one antipsychotic agent in the manufacture of a medicament for simultaneous therapeutic administration in the treatment of a psychotic disorder. The invention further provides a combination of compounds of formula (I) or a pharmaceutically acceptable salt thereof and at least one antipsychotic agent for simultaneous therapeutic administration in the treatment of a psychotic disorder. The invention further provides the use of compounds of formula (I) or a pharmaceutically acceptable salt thereof in the manufacture of a medicament for simultaneous therapeutic administration with at least one antipsychotic agent in the treatment of a psychotic disorder. The invention further provides compounds of formula (I) or a pharmaceutically acceptable salt thereof for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) or a pharmaceutically acceptable salt thereof in the treatment of a psychotic disorder. The invention further provides at least one antipsychotic agent for simultaneous therapeutic administration with compounds of formula (I) or a pharmaceutically acceptable salt thereof in the treatment of a psychotic disorder.

In a further aspect, the invention provides a kit-of-parts for use in the treatment of a psychotic disorder comprising a first dosage form comprising compounds of formula (I) or a pharmaceutically acceptable salt thereof and one or more further dosage forms each comprising an antipsychotic agent for simultaneous therapeutic administration.

In another aspect, the invention provides a method of treatment of a psychotic disorder by adjunctive therapeutic administration of a compound of the present invention to a patient receiving therapeutic administration of an active ingredient selected from the group consisting of: a mood stabiliser, an antidepressant, an anxiolytic, a drug for extrapyrimidal side effects and a cognitive enhancer.

In a further aspect, the invention provides the use of a compound of the present invention in the manufacture of a medicament for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention also provides a compound of the present invention for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention also provides the use of a compound of the present invention in adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention further provides the use of a compound of the present invention for use for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

In a further aspect, the invention provides a method of treatment of a psychotic disorder by adjunctive therapeutic administration of an active ingredient selected from the group consisting of: a mood stabiliser, an antidepressant, an anxiolytic, a drug for extrapyrimidal side effects and a cognitive enhancer to a patient receiving therapeutic administration of a compound of the present invention.

In a further aspect, the invention provides the use of an active ingredient selected from the group consisting of: a mood stabiliser, an antidepressant, an anxiolytic, a drug for extrapyrimidal side effects and a cognitive enhancer in the manufacture of a medicament for adjunctive therapeutic administration for the treatment of a psychotic disorder in a patient receiving therapeutic administration of a compound of the present invention.

The invention also provides an active ingredient selected from the group consisting of: a mood stabiliser, an antidepressant, an anxiolytic, a drug for extrapyrimidal side effects and a cognitive enhancer for adjunctive therapeutic administration for the treatment of a psychotic disorder in a patient receiving therapeutic administration of a compound of the present invention The invention also provides the use of an active ingredient selected from the group consisting of: a mood stabiliser, an antidepressant, an anxiolytic, a drug for extrapyrimidal side effects and a cognitive enhancer for adjunctive therapeutic administration for the treatment of a psychotic disorder in a patient receiving therapeutic administration of a compound of the present invention In a further aspect, the invention provides a method of treatment of a psychotic disorder by simultaneous therapeutic administration of a compound of the present invention in combination with an active ingredient selected from the group consisting of: a mood stabiliser, an antidepressant, an anxiolytic, a drug for extrapyrimidal side effects and a cognitive enhancer.

The invention further provides the use of a combination of a compound of the present invention and an active ingredient selected from the group consisting of: a mood stabiliser, an antidepressant, an anxiolytic, a drug for extrapyrimidal side effects and a cognitive enhancer in the manufacture of a medicament for simultaneous therapeutic administration in the treatment of a psychotic disorder.

The invention further provides a combination of a compound of the present invention and an active ingredient selected from the group consisting of: a mood stabiliser, an antidepressant, an anxiolytic, a drug for extrapyrimidal side effects and a cognitive enhancer for simultaneous therapeutic administration for the treatment of a psychotic disorder.

The invention further provides the use of a combination of a compound of the present invention and an active ingredient selected from the group consisting of: a mood stabiliser, an antidepressant, an anxiolytic, a drug for extrapyrimidal side effects and a cognitive enhancer for simultaneous therapeutic administration in the treatment of a psychotic disorder.

The invention further provides the use of a compound of the present invention in the manufacture of a medicament for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides a compound of the present invention for simultaneous therapeutic administration with an active ingredient selected from the group consisting of: a mood stabiliser, an antidepressant, an anxiolytic, a drug for extrapyrimidal side effects and a cognitive enhancer for the treatment of a psychotic disorder.

The invention further provides the use of a compound of the present invention for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides a compound of the present invention for use for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides the use of an active ingredient selected from the group consisting of: a mood stabiliser, an antidepressant, an anxiolytic, a drug for extrapyrimidal side effects and a cognitive enhancer in the manufacture of a medicament for simultaneous therapeutic administration with a compound of the present invention in the treatment of a psychotic disorder.

The invention further provides an active ingredient selected from the group consisting of: a mood stabiliser, an antidepressant, an anxiolytic, a drug for extrapyrimidal side effects and a cognitive enhancer for simultaneous therapeutic administration with a compound of the present invention for the treatment of a psychotic disorder.

The invention further provides the use of an active ingredient selected from the group consisting of: a mood stabiliser, an antidepressant, an anxiolytic, a drug for extrapyrimidal side effects and a cognitive enhancer for simultaneous therapeutic administration with a compound of the present invention in the treatment of a psychotic disorder.

In a further aspect, the invention provides a kit-of-parts for use in the treatment of a psychotic disorder comprising a first dosage form comprising a compound of the present invention and one or more further dosage forms each comprising an active ingredient selected from the group consisting of: a mood stabiliser, an antidepressant, an anxiolytic, a drug for extrapyrimidal side effects and a cognitive enhancer for simultaneous therapeutic administration.

In one embodiment, the patient is a human.

Examples of antipsychotic drugs that may be useful in the present invention include, but are not limited to: sodium channel blockers; mixed 5HT/dopamine receptor antagonists; mGluR5 positive modulators; D3 antagonists; 5HT6 angatonists; nicotinic alpha-7 modulators; glycine transporter GlyT1 inhibitors; D2 partial agonist/D3 antonogist/H3 antagonists; AMPA modulators; NK3 antagonists such as osanetant and talnetant; an atypical antipsychotic, for example clozapine, olanzapine, risperidone, quetiapine, aripirazole, ziprasidone and amisulpride; butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs that may be suitable for use in the present invention are as follows: clozapine (available under the tradename CLOZARIL®, from Mylan, Zenith Goldline, UDL, Novartis); olanzapine (available under the tradename ZYPREXA®, from Lilly); ziprasidone (available under the tradename GEODON®, from Pfizer); risperidone (available under the tradename RISPERDAL®, from Janssen); quetiapine fumarate (available under the tradename SEROQUEL®, from AstraZeneca); sertindole (available under the tradename SERLECT®); amisulpride (available under the tradename SOLION®, from Sanofi-Synthelabo); haloperidol (available under the tradename HALDOL®, from Ortho-McNeil); haloperidol decanoate (available under the tradename HALDOL Decanoate®); haloperidol lactate (available under the tradenames HALDOL® and INTENSOL®); chlorpromazine (available under the tradename THORAZINE®, from SmithKline Beecham (GSK)); fluphenazine (available under the tradename PROLIXIN®, from Apothecon, Copley, Schering, Teva, and American Pharmaceutical Partners, Pasadena); fluphenazine decanoate (available under the tradename PROLIXIN Decanoate®); fluphenazine enanthate (available under the tradename PROLIXIN®); fluphenazine hydrochloride (available under the tradename PROLIXIN®); thiothixene (available under the tradename NAVANE®, from Pfizer); thiothixene hydrochloride (available under the tradename NAVANE®); trifluoperazine (10-[3-(4-methyl-1-piperazinyl)propyl]-2-(trifluoromethyl)phenothiazine dihydrochloride, available under the tradename STELAZINE®, from SmithKline Beckman); perphenazine (available under the tradename TRILAFON®, from Schering); perphenazine and amitriptyline hydrochloride (available under the tradename ETRAFON TRILAFON®); thioridazine (available under the tradename MELLARIL®; from Novartis, Roxane, HiTech, Teva, and Alpharma); molindone (available under the tradename MOBAN®, from Endo); molindone hydrochloride (available under the tradename MOBAN®); loxapine (available under the tradename LOXITANE®; from Watson); loxapine hydrochloride (available under the tradename LOXITANE®); and loxapine succinate (available under the tradename LOXITANE®). Furthermore, benperidol (Glianimon®), perazine (Taxilan®) or melperone (Eunerpan®)) may be used.

Other suitable antipsychotic drugs include promazine (available under the tradename SPARINE®), triflurpromazine (available under the tradename VESPRIN®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), iloperidone, pimozide and flupenthixol.

The antipsychotic drugs listed above by Tradename may also be available from other suppliers under a different Tradename.

In one further aspect of the invention, suitable antipsychotic agents include olanzapine, risperidone, quetiapine, amisulpride, aripiprazole, haloperidol, clozapine, olanzepine, ziprasidone, talnetant and osanetant.

Mood stabilisers which may be used in the therapy of the present invention include lithium, sodium valproate/valproic acid/divalproex, carbamazepine, lamotrigine, gabapentin, topiramate, oxcarbazepine and tiagabine.

Antidepressant drugs which may be used in the therapy of the present invention include serotonin antagonists, CRF-1 antagonists, Cox-2 inhibitor/SSRI dual antagonists; dopamine/noradrenaline/serotonin triple reuptake inhibitors; NK1 antagonists; NK1 and NK2 dual antagonists; NK1/SSRI dual antagonists; NK2 antagonists; serotonin agonists (such as rauwolscine, yohimbine and metoclopramide); serotonin reuptake inhibitors (such as citalopram, escitalopram, fluoxetine, fluvoxamine, femoxetine, indalpine, zimeldine, paroxetine and sertraline); dual serotonin/noradrenaline reuptake inhibitors (such as venlafaxine, reboxetine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); 5HT3 antagonists (such as example ondansetron and granisetron); and others (such as bupropion, amineptine, radafaxine, mianserin, mirtazapine, nefazodone and trazodone).

Anxiolytics which may be used in the therapy of the present invention include V1b antagonists, 5HT7 antagonists and benzodiazepines such as alprazolam and lorazepam.

Drugs for extrapyramidal side effects which may be used in the therapy of the present invention include anticholinergics (such as benztropine, biperiden, procyclidine and trihexyphenidyl), antihistamines (such as diphenhydramine) and dopaminergics (such as amantadine).

Cognitive enhancers which may be used in the therapy of the present invention include example cholinesterase inhibitors (such as tacrine, donepezil, rivastigmine and galantamine), H3 antagonists and muscarinic $M_1$ agonists (such as cevimeline).

For use in medicine, the compounds of the present invention are usually administered as a standard pharmaceutical composition. The present invention therefore provides in a further aspect a pharmaceutical composition comprising a compound of formula (I) as hereinbefore described or a pharmaceutically acceptable salt thereof and a pharmaceutically acceptable carrier. The pharmaceutical composition can be for use in the treatment of any of the conditions described herein. In a further aspect, the invention provides a process for preparing a pharmaceutical composition, the process comprising mixing a compound of formula (I) as hereinbefore described or a pharmaceutically acceptable salt thereof and one or more pharmaceutically acceptable carriers. In a further aspect, the invention provides a pharmaceutical composition comprising a compound of formula (I) as hereinbefore described or a pharmaceutically acceptable salt thereof in combination with at least 1 antipsychotic, and one or more pharmaceutically acceptable carriers. In a further aspect, the invention provides a process for preparing a pharmaceutical composition, the process comprising mixing a compound of formula (I) as hereinbefore described or a pharmaceutically acceptable salt thereof, at least 1 antipsychotic, and one or more pharmaceutically acceptable carriers.

The compounds of the invention may be administered by any convenient method, for example by oral, parenteral (e.g. intravenous), buccal, sublingual, nasal, rectal or transdermal administration and the pharmaceutical compositions adapted accordingly.

The compounds of the invention which are active when given orally can be formulated as liquids or solids, for example syrups, suspensions or emulsions, tablets, capsules and lozenges.

A liquid formulation will generally consist of a suspension or solution of the compound of the invention or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochloro-hydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. The composition may be in unit dose form such as a tablet, capsule or ampoule.

Each dosage unit for oral administration contains, for example, from 1 to 250 mg (and for parenteral administration contains, for example, from 0.1 to 25 mg) of a compound of the formula (I) or a pharmaceutically acceptable salt thereof calculated as the free base.

The daily dosage contains suitably from 0.01 mg/kg to 100 mg/kg of a compound of formula (I) or a pharmaceutically acceptable salt thereof calculated as the free base.

It will be appreciated that the precise dose administered will depend on the age and condition of the patient and the frequency and route of administration and will be at the ultimate discretion of the attendant physician.

The antipsychotic agent component or components used in the adjunctive therapy of the present invention may also be administered in their basic or acidic forms as appropriate or, where appropriate, in the form of a pharmaceutically acceptable salt or other derivative. All solvates and all alternative physical forms of the antipsychotic agent or agents or their salts or derivatives as described herein, including but not limited to alternative crystalline forms, amorphous forms and polymorphs, are also within the scope of this invention. In the case of the antipsychotic agent or agents, the forms and derivatives are, for example, those which are approved for therapeutic administration as monotherapies, including those mentioned above, but all references to antipsychotic agents herein include all salts or other derivatives thereof, and all solvates and alternative physical forms thereof.

For adjunctive therapeutic administration according to the invention, compounds of formula (I) or pharmaceutically acceptable salts thereof and the antipsychotic agent or agents or their salts, derivatives or solvates may each be administered in pure form, but each of the components will, for example, be formulated into any suitable pharmaceutically acceptable and effective composition which provides effective levels of the respective component in the body. The choice of the most appropriate pharmaceutical compositions for each component is within the skill of the art, and may be the same form or different forms for each of the components. Suitable formulations include, but are not limited to tablets, capsules, powders, granules, lozenges, suppositories, reconstitutable powders, or liquid preparations such as oral or sterile parenteral solutions or suspensions.

For simultaneous administration as a combined composition of compounds of formula (I) and the antipsychotic agent or agents according to the invention, compounds of formula (I) or their pharmaceutically acceptable salts and the antipsychotic agent or agents and their salts, derivatives or solvates may be administered together in pure form, but the combined components will, for example, be formulated into any suitable pharmaceutically acceptable and effective composition which provides effective levels of each of the components in the body. The choice of the most appropriate pharmaceutical compositions for the combined components is within the skill of the art. Suitable formulations include, but are not limited to tablets, sub-lingual tablets, buccal compositions, capsules, powders, granules, lozenges, suppositories, reconstitutable powders, or liquid preparations such as oral or sterile parenteral solutions or suspensions.

In order to obtain consistency of adjunctive administration, the compositions of each of the components, or of the combination of the components is, for example, in the form of a unit dose.

The term "treatment" includes prophylaxis, where this is appropriate for the relevant condition(s).

Biological Test Methods

FLIPR Experiments on $M_1$ Receptors to Determine Agonist/Antagonist Potency

Compounds of the invention were characterized in a functional assay to determine their ability to activate the intracellular calcium pathway in CHO cells with stable expression of human muscarinic $M_1$ receptors using FLIPR (Fluorometric Imaging Plate Reader) technology. Briefly, CHO-$M_1$ cells were plated (15,000/well) and allowed to grow overnight at 37 degrees. Media were removed and 30 µL loading buffer (HBSS with 2.5 mM probenicid, 2 µM Fluo-4, 500 µM Brilliant Black, pH 7.4) was added. After incubation at 37 degrees for 90 minutes, 10 µL of the assay buffer (HBSS with 2.5 mM probenecid, pH 7.4) containing test compounds was added to each well on the FLIPR instrument. Calcium response was monitored to determine agonism. Plates were then incubated for another 30 minutes before 10 µL of assay buffer containing acetylcholine was added at an $EC_{80}$, as the agonist challenge. Calcium response was then monitored again to determine compound's antagonism to acetylcholine. Concentration-response curves of both agonism and antagonism on $M_1$ receptors were performed for each compound. Results were imported into ActivityBase data analysis suite (ID Business Solution Inc., Parsippany, N.J.) where the curves were analysed by non-linear curve fitting and the resulting $pEC_{50}$/fpKi were calculated. The maximum asymptotes of agonist compounds were calculated as percentage of maximum FLIPR response induced by carbamoylcholine chloride added as control on the same compound plates.

The example compounds below were tested in the above assay and were found to have average $pEC_{50}$ values of >5.8 at the muscarinic $M_1$ receptor, and intrinsic activity >50%.

FLIPR Experiments on $M_{2-5}$ Receptor to Determine Receptor Subtype Selectivity To determine selectivity of compounds of the invention against other muscarinic receptor subtypes, compounds were characterized in FLIPR experiments in CHO cells with stable expression of human muscarinic receptors, $M_2$, $M_3$, $M_4$ or $M_5$. In the case of $M_2$ and $M_4$ receptors, chimeric G-protein Gqi5 was also co-expressed to couple receptors to the calcium signalling pathway. Briefly, cells were plated (15,000/well) and allowed to grow overnight at 37 degrees. The FLIPR experiment was then carried out on the next day using the same protocol as described above for CHO-M1 cells. Results were imported into ActivityBase data analysis suite where the curves were analysed by non-linear curve fitting and the resulting $pEC_{50}$/fpKi values were calculated.

The example compounds below were tested in the $M_{2-5}$ receptor assays and the majority of the examples were found to be selective for the $M_1$ receptor over $M_2$, $M_3$, $M_4$ and $M_5$ receptors, with typical selectivity (ratio of $pEC_{50}$'s) of $\geq$10-fold, and in certain cases $\geq$100-fold.

The invention is further illustrated by the following non-limiting examples. In the procedures that follow, after each starting material, reference to a Description by number is typically provided. This is provided merely for assistance to the skilled chemist. The starting material may not necessarily have been prepared from the batch referred to.

SCX columns (including SCX, SCX-2, SCX-3) refer to sulfonic acid ion exchange resins supplied by Varian, IST and Radleys.

Amino doped silica columns are supplied by Biotage

SPE-Si cartridges are silica solid phase extraction columns supplied by Varian.

Flash silica gel chromatography was carried out on, for example, silica gel 230-400 mesh (supplied by Merck AG Darmstadt, Germany) or over pre-packed Biotage silica cartridges (e.g. 12+M, or 65i) on Biotage Horizon, SP1 or SP4 machines.

For specified hydrogenation reactions, an H-cube was used. The H-cube is a continuous flow hydrogenator developed by Thales Nanotechnology. A solution of the sample to be hydrogenated is delivered to the reactor in a continuous stream using an HPLC pump. In the reactor it is mixed with hydrogen (generated from electrolysis of water), heated, and passed through a catalyst (e.g. palladium on charcoal) cartridge (up to 100° C. and 100 bar pressure) to produce a continuous flow of hydrogenated product.

NMR spectra were obtained at 298K, at the frequency stated using either a Bruker™ DPX400 or an Oxford Instruments™ 250 MHz machine and run as a dilute solution of CDCl$_3$ unless otherwise stated. All NMR spectra were reference to tetramethylsilane (TMS $\delta_H$ 0, $\delta_C$ 0). All coupling constants are reported in hertz (Hz), and multiplicities are labelled s (singlet), bs, (broad singlet), d (doublet), t (triplet), q (quartet), dd (doublet of doublets), dt (doublet of triplets) and m (multiplet). NMR spectral data, where provided, were obtained for the title substance in each Description or Example (e.g. the hydrochloride salt, or the free base), unless otherwise stated.

Mass spectra (MS) were taken on a 4 II triple quadropole Mass Spectrometer (Micromass UK) or on a Agilent MSD 1100 Mass Spectrometer, operating in ES (+) and ES (−) ionization mode or on a Agilent LC/MSD 1100 Mass Spectrometer, operating in ES (+) and ES (−) ionization mode coupled with HPLC instrument Agilent 1100 Series [LC/MS-ES (+)]. Analysis was performed on a Waters Atlantis column (50×4.6 mm) with a stationary phase particle size of 3 μM. Mobile phase A (aqueous phase)=water+0.05% formic acid; mobile phase B (organic solvent)=acetonitrile+0.05% formic acid.

Method as follows:

| Time/min | % A | % B |
|----------|-----|-----|
| 0        | 97  | 3   |
| 0.1      | 97  | 3   |
| 4        | 3   | 97  |
| 4.8      | 3   | 97  |
| 4.9      | 97  | 3   |
| 5.0      | 97  | 3   |

The above method had a flow rate of 3 mL/min. The injection volume was 54. The column temperature was 30° C. The UV detection range was from 220 to 330 nm.

MDAP (mass-directed auto-preparation) refers to purification by HPLC on a Waters machine, wherein fraction collection is triggered by detection of the programmed mass ion for the compound of interest. High pH separations refer to use of a water/acetonitrile/ammonium carbonate gradient.

For reactions involving microwave irradiation, a Biotage Initiator was used.

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities ranging from for example 85% to 98%. However, calculations of number of moles and yield are generally not adjusted for this.

ABBREVIATIONS

NMR Nuclear Magnetic Resonance
THF tetrahydrofuran
DMSO dimethylsulfoxide
DMF dimethylformamide
DCM dichloromethane
EDC 1-ethyl-3-(dimethylaminopropyl)carbodiimide
Et$_2$O diethyl ether
HOBt 1-hydroxybenzotriazole
MeOH methanol
DIPEA (Hunig's base)diisopropylethylamine
EtOAc ethyl acetate
MDAP Mass-Directed Auto-Preparation
sat saturated
LC/MS liquid chromatography/mass spectrometry
Rt/rt/room temp room temperature
Pd/C palladium on charcoal All starting materials are commercially available, unless indicated otherwise.

Description 1. 1,1-Dimethylethyl 4-[(4-fluoro-2-hydroxy-5-methylphenyl)amino]-1-piperidine carboxylate (D1)

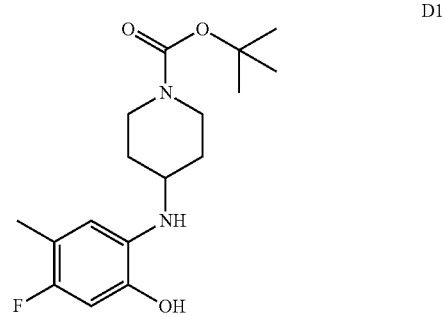 [SMILES: Cc1cc(NC2CCN(C(=O)OC(C)(C)C)CC2)c(O)cc1F]

Polymer supported sodium cyanoborohydride (794 mg, 3.41 mmol) was added to a solution of commercially available 2-amino-5-fluoro-4-methylphenol (241 mg, 1.71 mmol), 1,1-dimethylethyl 4-oxo-1-piperidinecarboxylate (350 mg, 1.76 mmol) and acetic acid (0.489 mL, 8.53 mmol) in dichloromethane (10 mL). The mixture was heated by microwave at 100° C. for 30 min before being filtered and concentrated by rotary evaporation to give a green oil. The residue was purified via chromatography (silica, dichloromethane to 0.5% ammonia/9.5% methanol/90% dichloromethane) to give 1,1-dimethylethyl 4-[(4-fluoro-2-hydroxy-5-methylphenyl)amino]-1-piperidinecarboxylate (593 mg, 73% purity, 78% yield) as a brown oil.

MH+325.

Description 2. 1,1-Dimethylethyl 4-(6-fluoro-5-methyl-2-oxo-1,3-benzoxazol-3(2H)-yl)-1-piperidinecarboxylate (D2)

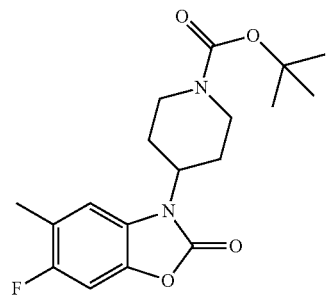

D2

Hünig's base (0.5 mL, 2.86 mmol) was added to a solution of 1,1-dimethylethyl 4-[(4-fluoro-2-hydroxy-5-methylphenyl)amino]-1-piperidinecarboxylate (D1, 593 mg, 1.34 mmol) in dichloromethane (10 mL) at rt under argon. The reaction was cooled to 0° C. and the triphosgene (167 mg, 0.564 mmol) was added. The reaction was then stirred for 1.5 h at 0° C. and quenched with saturated aqueous NaHCO₃ (10 mL) before being partitioned between dichloromethane and water. The aqueous layer was extracted with dichloromethane (2×) and the combined organics were dried (Na₂SO₄) and concentrated by rotary evaporation to give an orange oil. The residue was purified via chromatography (silica, dichloromethane to 0.5% ammonia/9.5% methanol/90% dichloromethane) to give 1,1-dimethylethyl 4-(6-fluoro-5-methyl-2-oxo-1,3-benzoxazol-3(2H)-yl)-1-piperidine carboxylate (D2, 546 mg, 73% purity, 85% yield) as an orange oil.

M-$^t$Bu+2H+ 295.

Description 3. 6-Fluoro-5-methyl-3-(4-piperidinyl)-1,3-benzoxazol-2(3H)-one (D3)

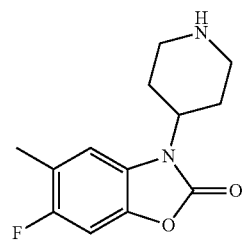

D3

1,1-Dimethylethyl 4-(6-fluoro-5-methyl-2-oxo-1,3-benzoxazol-3(2H)-yl)-1-piperidine carboxylate (D2, 546 mg, 1.14 mmol) was dissolved in dichloromethane (10 mL) at rt. HCl (10 mL, 40 mmol, 4 M in 1,4-dioxane) was added and the reaction was stirred overnight. It was then concentrated by rotary evaporation to give a pale brown solid. The residue was dissolved in methanol/dichloromethane and purified by SCX (5 g, eluting with methanol, followed by 2 M ammonia in methanol). The ammonia/methanol fraction was concentrated by rotary evaporation to give 6-fluoro-5-methyl-3-(4-piperidinyl)-1,3-benzoxazol-2(3H)-one (D3, 318 mg, 72% purity, 80% yield) as an orange oil.

MH+ 251.

Description 4. 4-[4-(6-fluoro-5-methyl-2-oxo-1,3-benzoxazol-3(2H)-yl)-1-piperidinyl]tetrahydro-2H-pyran-4-carbonitrile (D4)

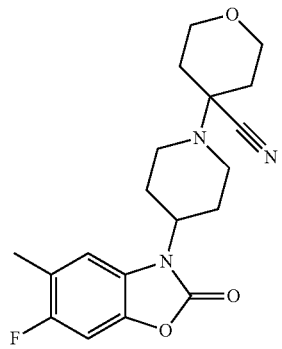

D4

6-Fluoro-5-methyl-3-(4-piperidinyl)-1,3-benzoxazol-2(3H)-one (D3, 318 mg, 0.915 mmol) was dissolved in N,N-dimethylacetamide (10 mL) at rt under argon. Magnesium sulfate (562 mg, 4.67 mmol), acetone cyanohydrin (0.17 mL, 1.86 mmol) and tetrahydro-4H-pyran-4-one (0.17 mL, 1.84 mmol) were added and the reaction was heated at 70° C. for 24 h under a gentle stream of argon. The mixture was then cooled to rt, diluted with 1:1 dichloromethane:water (30 mL) and sonicated for 20 min. The phases were allowed to separate and the organic phase was dried by filtering through a hydrostatic cartridge. A further 10 mL of dichloromethane was added to the aqueous phase and the mixture stirred vigorously for 10 min. The 2 phases were again separated and the organic phase was dried by filtering through a hydrostatic cartridge. The combined organic layers were concentrated by rotary evaporation to give 4-[4-(6-fluoro-5-methyl-2-oxo-1,3-benzoxazol-3(2H)-yl)-1-piperidinyl]tetrahydro-2H-pyran-4-carbonitrile (D4, 681 mg, 45% purity, 93% yield) as an orange solid.

M-CN+ 333.

Description 5. 5-Fluoro-4-methyl-2-{[1-(4-methyltetrahydro-2H-pyran-4-yl)-4-piperidinyl]amino}phenol (D5)

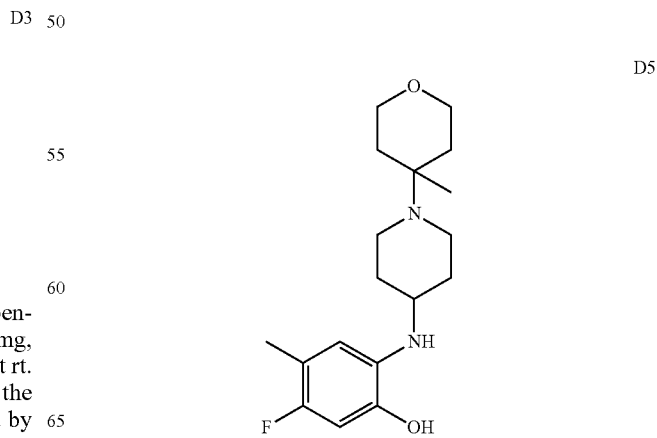

D5

Methylmagnesium iodide (3 mL, 9 mmol, 3 M in diethyl ether) was added to a suspension of 4-[4-(6-fluoro-5-methyl-2-oxo-1,3-benzoxazol-3(2H)-yl)-1-piperidinyl]tetrahydro-2H-pyran-4-carbonitrile (D4, 681 mg, 0.852 mmol) in tetrahydrofuran (10 mL) at 0° C. under argon. The reaction was stirred for 1 h at rt before being cooled to 0° C. and quenched with saturated aqueous NH$_4$Cl (5 mL). The mixture was partitioned between ethyl acetate and water and the aqueous layer was extracted with ethyl acetate. The combined organics were dried (Na$_2$SO$_4$) and concentrated by rotary evaporation to give a brown oil, which was purified via chromatography (silica, dichloromethane to 0.5% ammonia/9.5% methanol/90% dichloromethane) to give a brown oil. This was further purified by high pH MDAP to give 5-fluoro-4-methyl-2-{[1-(4-methyltetrahydro-2H-pyran-4-yl)-4-piperidinyl]-amino}phenol (D5, 47 mg 17% yield) as a brown solid.

MH$^+$ 323.

Description 6. 6-Fluoro-3-(4-piperidinyl)-1,3-benzoxazol-2(3H)-one. (D6)

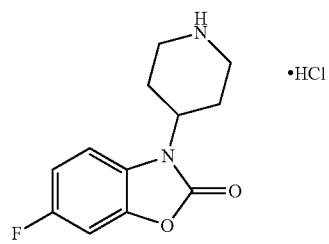

The title compound D6 was prepared as described in U.S. Pat. No. 5,238,908.

Description 7. 2-Amino-4-(trifluoromethyl)phenol. (D7)

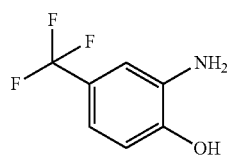

A solution of 2-nitro-4-(trifluoromethyl)phenol (100 mg, 0.483 mmol) in ethanol (10 mL) was pumped through an H-cube™ hydrogenator CatCart (Pd/C, 30×4 mm) at a flow rate of 1 mL/min at 40° C. and 40 psi, topping up the solution with methanol (10×1 mL) when it was running low. The collected solution was evaporated to dryness to give an off-white solid (88 mg, assume quantitative yield). The material was carried forward without further purification.

(M+H)$^+$=178.

$^1$H NMR δ (CDCl$_3$): 6.76 (1H, d, J=8.4 Hz), 6.94 (1H, d, J=8.4 Hz), 6.98 (1H, s).

Description 8. tetrahydro-2H-pyran-4-carboxylic acid (D8)

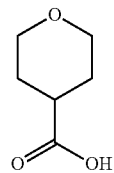

Sodium hydroxide (7.05 mL, 12.5 M, 88 mmol) was added dropwise to a solution of methyl tetrahydro-2H-pyran-4-carboxylate (2.54 g, 17.6 mmol) in a mix of methanol (30 mL) and THF (30 mL) at 25° C. The reaction was stirred over the weekend. The THF/MeOH was then evaporated and the crude was washed with Et$_2$O (2×). The aqueous layer was acidified and extracted with EtOAc (2×); the organics were dried over Na$_2$SO$_4$, filtered and the solvent was evaporated to give the title compound (D8) (1.94 g, 76%) as a white solid.

Description 9. 4-methyltetrahydro-2H-pyran-4-carboxylic acid. (D9)

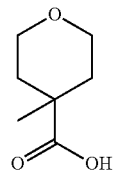

Diisopropylamine (6.37 mL, 44.7 mmol) in THF (50 mL) was cooled to 0° C. under argon. N-Butyllithium (16.7 mL, 2.5 M in hexane, 41.7 mmol) was added dropwise over 10 min. The reaction mixture was left to stir for 15 min at 0° C. A solution of tetrahydro-2H-pyran-4-carboxylic acid (D8) (1.94 g, 14.9 mmol) in THF (10 mL) was added and a white precipitate was formed. The resulting mixture was then heated at 50° C. for 3 h. The reaction mixture was cooled to 0° C. and methyl iodide (2.80 mL, 44.7 mmol) was added dropwise. The reaction was then allowed to warm to rt and left to stir overnight. 10% aqueous citric acid solution (40 mL) was then added and the THF was removed by rotary evaporation. The residual aqueous mixture was extracted with Et$_2$O (2×). The organics were combined, dried (Na$_2$SO$_4$) and concentrated by rotary evaporation to give the title compound (D9) (1.26 g, 53%) as a yellow solid.

Description 10. 4-isocyanato-4-methyltetrahydro-2H-pyran. (D10)

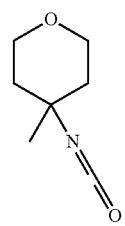

A stirred solution of 4-methyltetrahydro-2H-pyran-4-carboxylic acid (D9) (1.26 g, 8.74 mmol) in Toluene (50 mL) at room temperature under argon was treated with triethylamine (1.58 mL, 11.36 mmol) and diphenyl azidophosphate (1.88 mL, 8.74 mmol) and heated to 85° C. for 2 hr. The mixture was allowed to cool to room temperature, then treated with 1 M NaOH solution (40 mL) and extracted with Et$_2$O (3×). The combined extract was dried (Na$_2$SO$_4$), filtered and concentrated under vacuum to give the title compound (D10) (520 mg, 34%) as a yellow oil.

Description 11.
4-methyltetrahydro-2H-pyran-4-amine hydrochloride (D11)

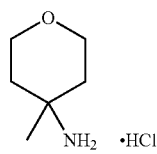

A solution of 4-isocyanato-4-methyltetrahydro-2H-pyran (D10) (520 mg, 3.68 mmol) in THF (30 mL) was treated with 5 M hydrochloric acid (4.05 mL, 20.3 mmol) and stirred at room temperature overnight. The mixture was then concentrated under vacuum to yield the title compound (D11) (820 mg, 3.52 mmol, 95% yield) as a pale green solid.

Description 12. 1-(4-methyltetrahydro-2H-pyran-4-yl)-4-piperidinone. (D12)

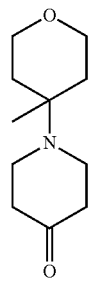

A stirred solution of 4-methyltetrahydro-2H-pyran-4-amine hydrochloride (D11) (640 mg, 4.22 mmol) in ethanol (20 mL) and H$_2$O (10 mL) at room temperature was treated with potassium carbonate (417 mg, 3.02 mmol) and the stirring was maintained for 10 min under argon. The mixture was then heated to 85° C. and a solution of 1-ethyl-1-methyl-4-oxopiperidinium iodide (D13, 1.11 g, 4.11 mmol) in a mix of ethanol/H$_2$O (8 mL, 1:1) was added over 15 min. The mixture was then refluxed for 2 extra hours. The mixture was then cooled to room temperature and poured onto an aqueous saturated solution of NaHCO$_3$. The aqueous obtained was extracted with DCM (3×). Organics were combined and washed with H$_2$O (1×), dried over Na$_2$SO$_4$, filtered and concentrated under vacuum. The crude product was then purified via chromatography (silica, DCM to 5% MeOH/95% DCM). The title compound (D12) (322 mg, 37%) was obtained as a yellow solid.

Description 13. 1-Ethyl-1-methyl-4-oxopiperidinium iodide. (D13)

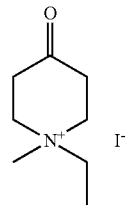

Iodomethane (65 mL; 1.00 mol) was added in portions to a solution of 1-ethyl-4-piperidone (100 g; 0.79 mol) in acetone (1 L) at 20-30° C. (internal, ice cooling). After stirring for 3 h more the title compound (D13) was obtained by filtration washing with acetone (189 g).

Description 14. 2-{[1-(4-Methyltetrahydro-2H-pyran-4-yl)-4-piperidinyl]amino}-4-(trifluoromethyl)phenol. (D14)

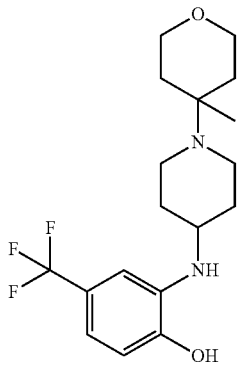

Polymer supported cyanoborohydride (191 mg, 0.82 mmol) was added to a solution of 1-(4-methyltetrahydro-2H-pyran-4-yl)-4-piperidinone (D12, 87 mg, 0.44 mmol), 2-amino-4-(trifluoromethyl)phenol (D7, 74 mg, 0.42 mmol, 4.3 mmol/g) and acetic acid (0.12 mL, 2.09 mmol) in DCM (2.5 mL). The mixture was heated by microwave at 100° C. for 10 min before being filtered and concentrated by rotary evaporation to give a yellow oil, which was purified via flash column chromatography (silica, DCM to 0.5% NH$_3$/9.5% MeOH/90% DCM) to give 2-{[1-(4-methyltetrahydro-2H-pyran-4-yl)-4-piperidinyl]amino}-4-(trifluoromethyl)phenol (D14, 89 mg, 60%) as an off-white solid.

LCMS: [M+H]$^+$ 359.

Description 15. 2-Fluoro-4-methyl-6-nitrophenol. (D15)

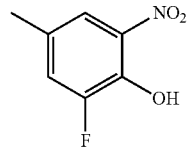

To 2-fluoro-4-methylphenol (500 mg, 3.96 mmol) in dichloromethane (5 mL) at room temperature was added dropwise nitric acid 70% (0.4 mL, 4.44 mmol) [exotherm observed]. After 15 min more washed with water, dried, evaporated to give 2-fluoro-4-methyl-6-nitrophenol D15 (400 mg, 2.337 mmol, 59.0% yield) as a yellow solid.

Description 16. 2-Fluoro-4-methyl-6-aminophenol (D16)

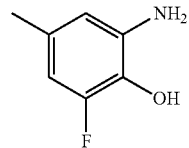

D16

A solution of 2-fluoro-4-methyl-6-nitrophenol (400 mg, 2.337 mmol) (D15) in ethanol (50 mL) was hydrogenated using a Pd/C cartridge in the H-cube™ hydrogenator at 1 mL/min and full hydrogen. Evaporation gave 2-fluoro-4-methyl-6-aminophenol (250 mg, 1.771 mmol, 76% yield) as a fawn solid.

Description 17. 2-Fluoro-4-methyl-6-{[1-(4-methyltetrahydro-2H-pyran-4-yl)-4-piperidinyl]amino}phenol. (D17)

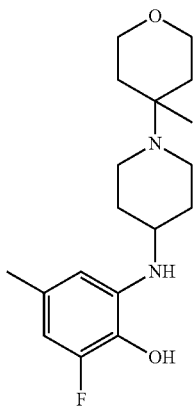

D17

2-Amino-6-fluoro-4-methylphenol (D16, 49 mg, 0.34 mmol) was dissolved in DCM (3 mL) and 1-(4-methyltetrahydro-2H-pyran-4-yl)-4-piperidinone (D12, 68 mg, 0.34 mmol), polymer supported cyanoborohydride (160 mg, 0.69 mmol, 4.3 mmol/g) and acetic acid (0.10 mL, 1.72 mmol) were all added at room temperature. The mixture was reacted at 100° C. in the microwave for 10 min. The mixture was then cooled to room temperature, filtered and the solvent was removed under vacuum to give the crude product, an orange oil, which was purified via flash column chromatography (silica, DCM to 0.5% NH$_3$/9.5% MeOH/90% DCM) to give 2-fluoro-4-methyl-6-{[1-(4-methyltetrahydro-2H-pyran-4-yl)-4-piperidinyl]amino}phenol (D17, 51 mg, 42%) as a white solid.

LCMS: [M+H]$^+$ 323.

EXAMPLE 1

6-Fluoro-5-methyl-3-[1-(4-methyltetrahydro-2H-pyran-4-yl)-4-piperidinyl]-1,3-benzoxazol-2(3H)-one hydrochloride (E1)

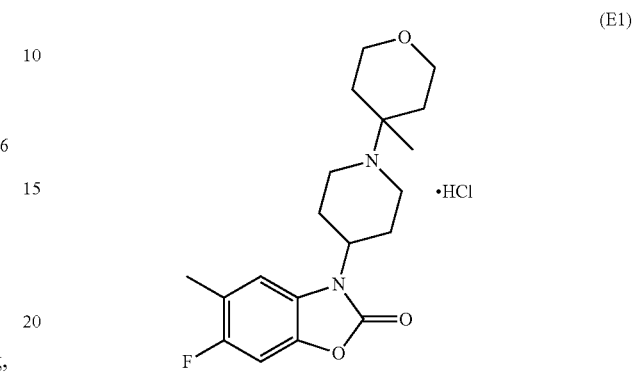

(E1)

Hünig's base (0.07 mL, 0.401 mmol) was added to a solution of 5-fluoro-4-methyl-2-{[1-(4-methyltetrahydro-2H-pyran-4-yl)-4-piperidinyl]amino}phenol (D5, 47 mg, 0.146 mmol) in dichloromethane (5 mL) at rt under argon. The reaction was cooled to 0° C., the triphosgene (22.8 mg, 0.077 mmol) was added and the mixture was stirred for 1 h at 0° C. The reaction was quenched with saturated aqueous NaHCO$_3$ (5 mL) and partitioned between dichloromethane and water. The aqueous layer was extracted with dichloromethane (2×) and the combined organics were dried (Na$_2$SO$_4$) and concentrated by rotary evaporation to give a brown oil. The crude residue was purified via chromatography (amino-doped silica, iso-hexane-ethyl acetate) to give the free base of the title compound as a white solid. HCl (0.05 mL, 0.05 mmol, 1 M in diethyl ether) was added to a solution of the free base in dichloromethane (0.5 mL). The solvent was removed by rotary evaporation and the resulting residue was triturated with diethyl ether (2×) to give 6-fluoro-5-methyl-3-[1-(4-methyltetrahydro-2H-pyran-4-yl)-4-piperidinyl]-1,3-benzoxazol-2(3H)-one hydrochloride (E1, 13.1 mg, 22% yield) as a white solid.

MH$^+$ 349

$^1$H NMR HCl salt δ (DMSO-d$_6$, 400 MHz) 1.39 (3H, s), 1.85 (2H, m), 2.00-2.11 (4H, m), 2.28 (3H, s), 2.76 (2H, m), 3.18 (2H, m), 3.43 (2H, m), 3.63 (2H, m), 3.90 (2H, m), 4.56 (1H, m), 7.38 (1H, d, J 9.2), 7.73 (1H, d, J 6.4), 10.01 (1H, m).

EXAMPLE 2

6-Fluoro-3-[1-(tetrahydro-2H-pyran-4-yl)-4-piperidinyl]-1,3-benzoxazol-2(3H)-one Hydrochloride. (E2)

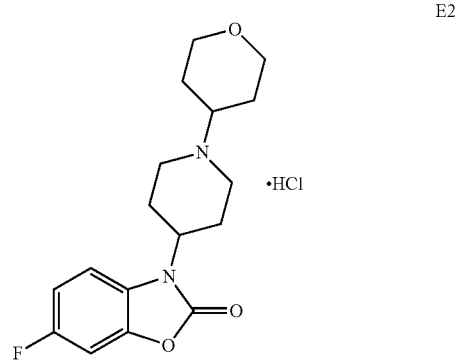 [SMILES: O=c1oc2cc(F)ccc2n1C1CCN(C2CCOCC2)CC1 ; Cl]

E2

A mixture of 6-fluoro-3-(4-piperidinyl)-1,3-benzoxazol-2 (3H)-one hydrochloride D6 (270 mg), tetrahydropyran-4-one (200 mg), and titanium tetraisopropoxide (0.6 mL) was stirred at room temperature for 1 h and then methanol (4 mL) and sodium cyanoborohydride (120 mg) were added. After a further 2 h the product was isolated by SCX chromatography and further purified by chromatography on silica gel eluting with 0-10% 2M methanolic ammonia-dichloromethane. Conversion to the hydrochloride salt gave 6-fluoro-3-[1-(tetrahydro-2H-pyran-4-yl)-4-piperidinyl]-1,3-benzoxazol-2 (3H)-one hydrochloride E2 (40 mg).

[M+H]$^+$ 321.

$^1$H NMR δ (DMSO-d$_6$, 250 MHz, HCl salt) 1.7 (2H, dq), 2.1 (4H, bt), 2.7 (2H, bq), 3.1-3.6 (7H, m), 4.0 (2H, dd), 4.5 (1H, m), 7.1 (1H, dt), 7.4 (1H, dd), 7.7 (1H, dd), and 10.6 (1 H, bs).

EXAMPLE 3

3-[1-(4-Methyltetrahydro-2H-pyran-4-yl)-4-piperidinyl]-5-(trifluoromethyl)-1,3-benzoxazol-2(3H)-one Hydrochloride. (E3)

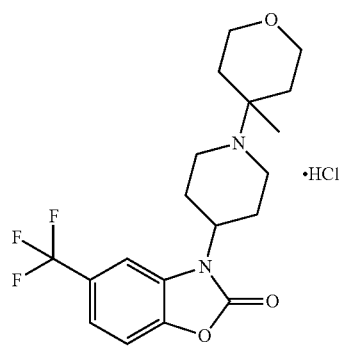

DIPEA (0.1 mL, 0.57 mmol) was added to a solution of 2-{[1-(4-methyltetrahydro-2H-pyran-4-yl)-4-piperidinyl] amino}-4-(trifluoromethyl)phenol (D14, 89 mg, 0.25 mmol) in DCM (5 mL) at rt under Ar. The reaction was cooled to 0° C. and the triphosgene (31 mg, 0.10 mmol) was added. The mixture was stirred for 3 h at 0° C. The reaction was quenched with sat. NaHCO$_3$ (5 mL) and partitioned between DCM and H$_2$O. The aqueous layer was extracted with DCM (2×) and the combined organics were dried (Na$_2$SO$_4$) and concentrated by rotary evaporation to give a pale yellow solid. The residue was purified via flash column chromatography (silica, DCM to 0.5% NH$_3$/9.5% MeOH/90% DCM) to give the free base of the title compound as a colourless oil. HCl (0.5 mL, 0.5 mmol, 1 M in Et$_2$O) was added to a solution of the free base in DCM (5 mL) and the reaction stirred for 30 min. The solvent was removed by rotary evaporation and the resulting solid triturated with Et$_2$O to give 3-[1-(4-methyltetrahydro-2H-pyran-4-yl)-4-piperidinyl]-5-(trifluoromethyl)-1,3-benzoxazol-2(3H)-one hydrochloride (E3, 81 mg, 73%) as a white solid.

$^1$H NMR HCl salt δ (DMSO-d$_6$, 400 MHz) 1.39 (3H, s), 1.81-1.88 (2H, m), 1.97-2.16 (4H, m), 2.70-2.83 (2H, m), 3.12-3.23 (2H, m), 3.42-3.51 (2H, m), 3.61-3.68 (2H, m), 3.86-3.93 (2H, m), 4.64 (1H, m), 7.53-7.60 (2H, m), 8.04 (1H, s), 10.09 (1H, m).

LCMS: [M+H]$^+$ 385.

EXAMPLE 4

7-Fluoro-5-methyl-3-[1-(4-methyltetrahydro-2H-pyran-4-yl)-4-piperidinyl]-1,3-benzoxazol-2(3H)-one Hydrochloride. (E4)

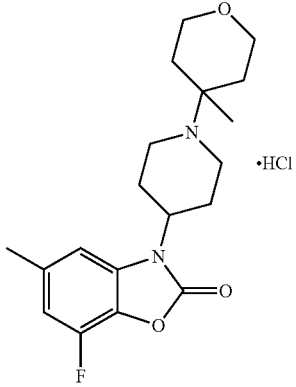

DIPEA (0.14 mL, 0.79 mmol) was added to a solution of 2-fluoro-4-methyl-6-{[1-(4-methyltetrahydro-2H-pyran-4-yl)-4-piperidinyl]amino}phenol (D17, 51 mg, 0.16 mmol) in DCM (5 mL) at room temperature under argon. The reaction was cooled to 0° C. and the triphosgene (19 mg, 0.07 mmol) was added. The mixture was stirred for 30 min at 0° C., followed by a further 15 min at room temperature. The reaction was quenched with sat. NaHCO$_3$ (5 mL) and partitioned between DCM and H$_2$O. The aqueous layer was extracted with DCM (2×) and the combined organics were dried (Na$_2$SO$_4$) and concentrated by rotary evaporation to give the crude product, which was purified via flash column chromatography (silica, DCM to 0.5% NH$_3$/9.5% MeOH/90% DCM) to give the free base of the title compound as a white solid. The free base was dissolved in DCM (2 mL) at 25° C. HCl (0.24 mL, 0.24 mmol, 1 M in Et$_2$O) was then added and the reaction was stirred for 15 min. The solvent was removed by rotary evaporation to give 7-fluoro-5-methyl-3-[1-(4-methyltetrahydro-2H-pyran-4-yl)-4-piperidinyl]-1,3-benzoxazol-2(3H)-one hydrochloride (E4, 47 mg, 70%) as a white solid.

$^1$H NMR HCl salt δ (DMSO-d$_6$, 400 MHz) 1.38 (3H, s), 1.81-1.87 (2H, m), 2.01-2.11 (4H, m), 2.37 (3H, s), 2.71-2.84 (2H, m), 3.13-3.25 (2H, m), 3.41-3.50 (2H, m), 3.58-3.66 (2 H, m), 3.86-3.93 (2H, m), 4.57 (1H, m), 6.96 (1H, d, J 11.5), 7.56 (1H, s), 10.16 (1H, m).

LCMS: [M+H]$^+$ 349.

The compound 1-[1-(tetrahydro-2H-pyran-4-yl)-4-piperidinyl]-1,3-dihydro-2H-indol-2-one hydrochloride can be made in a similar manner to the Examples above. 1-[1-(Tetrahydro-2H-pyran-4-yl)-4-piperidinyl]-1,3-dihydro-2H-indol-2-one hydrochloride was tested for activity but activity was below the threshold value.

The invention claimed is:
1. A compound of formula (I) or a salt thereof:

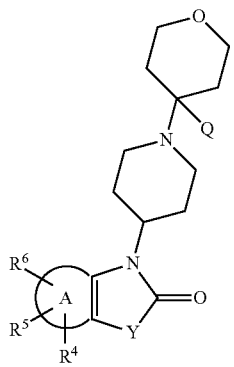

wherein:
$R^4$, $R^5$ and $R^6$ are independently selected from hydrogen, halogen, $C_{1-6}$alkyl, $C_{1-6}$alkyl substituted with one or more fluorine atoms, cyano, $C_{1-6}$alkylsulfonyl, $C_{1-6}$alkylsulfonyl substituted with one or more fluorine atoms, $C_{3-6}$cycloalkyl, $C_{1-6}$alkoxy, $C_{1-6}$alkoxy substituted with one or more fluorine atoms, $C_{1-6}$alkanoyl, —C(=NOC$_{1-6}$alkyl)C$_{1-6}$alkyl, $C_{1-6}$alkoxyC$_{1-6}$alkyl, and —C(O)NR$_a$R$_b$;
$R_a$ and $R_b$ are each independently hydrogen or $C_{1-6}$alkyl, or together with the nitrogen atom to which they are attached form a five or six membered ring;
ring A is a benzene ring or 6-membered aromatic heterocylic ring containing one or two nitrogen atoms;
Q is selected from hydrogen and $C_{1-6}$alkyl; and
Y is selected from O, S, $CH_2$, CHF, $CF_2$, CHMe, $C(Me)_2$, $CH_2CH_2$, $OCH_2$, and $CH_2O$.

2. A compound as claimed in claim 1 wherein $R^4$ is selected from hydrogen and halogen.
3. A compound as claimed in claim 1 wherein $R^5$ is selected from hydrogen and halogen.
4. A compound as claimed in claim 1 wherein $R^6$ is selected from hydrogen, $C_{1-2}$alkyl, and $C_{1-2}$alkyl substituted with one or more fluorine atoms.
5. A compound as claimed in claim 1 wherein Y is selected from O, S, $CH_2CH_2$, $OCH_2$, and $CH_2O$.
6. A compound as claimed in claim 1 wherein A is a benzene ring.
7. A compound as claimed in claim 1 wherein Q is selected from hydrogen and $C_{1-4}$-alkyl.
8. A compound as claimed in claim 1 which is selected from the group consisting of:
   6-Fluoro-5-methyl-3-[1-(4-methyltetrahydro-2H-pyran-4-yl)-4-piperidinyl]-1,3-benzoxazol-2(3H)-one;
   6-Fluoro-3-[1-(tetrahydro-2H-pyran-4-yl)-4-piperidinyl]-1,3-benzoxazol-2(3H)-one;
   3-[1-(4-Methyltetrahydro-2H-pyran-4-yl)-4-piperidinyl]-5-(trifluoromethyl)-1,3-benzoxazol-2(3H)-one; and
   7-Fluoro-5-methyl-3-[1-(4-methyltetrahydro-2H-pyran-4-yl)-4-piperidinyl]-1,3-benzoxazol-2(3H)-one
   and salts thereof.
9. A compound as claimed in claim 1 wherein the salt is a pharmaceutically acceptable salt.
10. A pharmaceutical composition comprising a compound as claimed in claim 9 and a pharmaceutically acceptable carrier.

* * * * *